United States Patent [19]

Zhou et al.

[11] Patent Number: 5,732,150
[45] Date of Patent: Mar. 24, 1998

[54] METHOD AND SYSTEM FOR MULTIPLE WAVELENGTH MICROSCOPY IMAGE ANALYSIS

[75] Inventors: Ruixia Zhou; Elizabeth H. Hammond, both of Salt Lake City; Dennis L. Parker, Centerville, all of Utah

[73] Assignee: IHC Health Services, Inc., Salt Lake City, Utah

[21] Appl. No.: 530,435

[22] Filed: Sep. 19, 1995

[51] Int. Cl.⁶ .................................................... G06K 9/00
[52] U.S. Cl. ........................ 382/133; 250/461.2; 382/164
[58] Field of Search .................... 250/461.2, 226; 356/39, 402, 414, 425; 358/500, 515; 364/413.08, 413.1, 413.11, 526; 377/10; 382/128, 133, 134, 164; 435/40.5, 40.51, 40.52, 240.1; 436/183

[56] References Cited

U.S. PATENT DOCUMENTS

| | | | |
|---|---|---|---|
| 3,919,530 | 11/1975 | Cheng | 364/413.08 |
| 4,191,940 | 3/1980 | Polcyn et al. | 340/146.3 |
| 4,601,537 | 7/1986 | Saccocio | 359/117 |
| 4,700,298 | 10/1987 | Palcic et al. | 364/413.1 |
| 4,724,543 | 2/1988 | Klevecz et al. | 382/133 |
| 4,887,892 | 12/1989 | Bacus | 382/133 |
| 4,998,284 | 3/1991 | Bacus et al. | 382/133 |
| 5,008,185 | 4/1991 | Bacus | 435/7.23 |
| 5,016,173 | 5/1991 | Kenet et al. | 382/128 |
| 5,107,422 | 4/1992 | Kamentsky et al. | 382/133 |
| 5,109,429 | 4/1992 | Bacus et al. | 346/183 |
| 5,121,436 | 6/1992 | Kasdan et al. | 382/128 |
| 5,124,932 | 6/1992 | Lodder | 364/498 |
| 5,134,662 | 7/1992 | Bacus et al. | 382/133 |
| 5,162,990 | 11/1992 | Odeyale et al. | 364/413.1 |
| 5,218,645 | 6/1993 | Bacus | 382/133 |
| 5,235,522 | 8/1993 | Bacus | 364/497 |
| 5,243,667 | 9/1993 | Hirosawa et al. | 382/233 |
| 5,287,272 | 2/1994 | Rutenberg et al. | 364/413.01 |
| 5,321,771 | 6/1994 | Burel | 382/108 |
| 5,428,690 | 6/1995 | Bacus et al. | 382/128 |
| 5,432,865 | 7/1995 | Kasdan et al. | 382/128 |
| 5,588,143 | 12/1996 | Stupek, Jr. et al. | 395/500 |

OTHER PUBLICATIONS

Bacus, S., J.L. Flowers, M.F. Press, J.W. Bacus and K.S. McCarty, "The Evaluation of Estrogen Receptor in Primary Breast Carcinoma by Computer–Assisted Image Analysis," A.J.C.P., vol. 90, No. 3, pp. 233–239, 1988.

Brugal, G., "Colour Processing in Automated Image Analysis for Cytology," in *Quantitative Image Analysis in Cancer Cytology and Histology*, J.Mary and J. Rigaut, Eds., Elsevier Science Publishers, B.V., 1986.

Brugal, G. C. Garbay, F. Giroud and D. Adelh, "A Double Scanning Microphotomer for Image Analysis: Hardware, Software and Biomedical Applications" J. Histochem. and Cytochem., vol. 27, No. 1, pp. 144–152, 1979.

(List continued on next page.)

*Primary Examiner*—Joseph Mancuso
*Assistant Examiner*—Marc Bobys
*Attorney, Agent, or Firm*—Eleanor V. Goodall; Mark G. Sandbaken

[57] ABSTRACT

A method and system for segmenting images of samples stained with two, three, or more stains accurately and reliably into multiple single-color images which represent the mass density of the stain at each position in the sample. The system includes a computer-controlled microscope and CCD camera, and at least one computer which includes data storage media for storing image data and which runs software for controlling image acquisition and analysis. To analyze tissue stained with N stains, images must be obtained at N different wavelengths, from multiply stained and singly stained samples. Relative stain mass densities are calculated with the use of the ratio of absorptivities measured at different wavelengths. The theoretical and practical basis for implementing the method with two, three, or more stains is presented. A method for selecting the wavelengths which provide optimal image accuracy and resolution is also provided.

10 Claims, 4 Drawing Sheets

OTHER PUBLICATIONS

Charpin, C., J. Jacquemier, L. Andrac, H. Vacheret, M.C. Habib, B. Devictor, M.N. Lavaut and M. Toga, "Multiparametric Analysis (SAMBA 200) of the Progesterone Receptor Immunocytochemical Assay in Nonmalignant and Malignant Breast Disorders," Am. J. Pathol., vol. 132, No. 2, pp. 199–211, 1988.

Charpin, C., L. Andrac, M.C. Habib, H. Vacheret, L. Xerpi, B. Devictor, M.N. Lavaut and M. Toga, "Immunodetection in Fine–Needle Aspirates and Multiparameteric (SAMBA) Image Analysis, " Cancer, vol. 63, pp. 863–872, 1989.

Charpin, C., P.M. Martin, B. Devictor, M.N. Lavaut, M.C. Habib, L. Andrac and M. Toga, "Multiparametric Study (SAMBA 200) of Estrogen Receptor Immunocytochemical Assay in 400 Human Breast Carcinomas: Analysis of Estrogen Receptor Distribution Heterogeneity in Tissues and Correlations with Dextran Coated Charcoal Assays and Morphological Data," Cancer Res., vol. 48, pp. 1578–1586, 1988.

Charpin, C., P.M. Martin, J. Jacquemier, M.N. Lavaut, N. Pourreau–Schnieder and M. Toga, "Estrogen Receptor Immunocytochemical Assay (ER–ICA): Computerized Image Analysis System, Immunoelectron Microscopy, and Comparisons with Estradial Binding Assays in 115 Breast Carcinomas," Cancer Res. (SUPPL)., vol. 46, pp. 4271s–4277s, 1986.

Chassery, J.M. and C. Garbay, "An Iterative Segmentation Method Based on a Contextural Color and Shape Criterion," IEEE Trans. Pattern Analysis and Machine Intelligence, vol. PAMI–6, No. 6, pp. 794–800, 1984.

Esteban, J.M., H. Battifora, Z. Warsi, A. Bailey and S. Bacus, "Quantification of Estrogen Receptors on Parraffin–Embedded Tumors by Image Analysis," Modern Pathol., vol. 4, pp. 53–57, 1991.

Figge, J., G. Bakst, D. Weisheit, O. Solis and J.S. Ross, "Image Analysis Quantitation of Immunoreactive Retinoblastoma Protein in Human Thyroid Neoplasms with a Streptavidin–biotin–peroxidase Staining Techniques," Am. J. Pathol., vol. 139, No. 6, pp. 1213–1219, 1991.

Garcia, J.A., J. Romero, L. Jimenez del Barco and E. Hita, "Improved Formula for Evaluating Colr–Differential Thresholds," Appl. Opt., vol. 31, No. 29, pp. 6292–6298, 1992.

Gauvain, C. D. Seigneurin and G. Brugal, "A Quantitative Analysis of the Human Bone Marrow Erythroblastic Cell Lineage Using the SAMBA 200 Cell Image Processor, I. The Normal Maturation Sequence," Analyt. Quant. Cytol. Histol., vol. 9, pp. 253–262, 1987.

Gillette, P.C., J.B. Lando and J.L. Koenig, "Computer–assisted Spectral Identification of Unknown Mixtures," Appl. Spectr., vol. 36, pp. 661–665, 1982.

Kasdan, H.L., K.C. Langford, J. Liberty, M. Zachariash and F. J. Deindoerfer, "High Performance Pathology Workstation using an Automated Multispectal Microscope," Applied Optics, vol. 26, No. 16, pp. 3294–3300, 1987.

Kawata, S. H. Komeda, K. Sasaki and S. Minami, "Advanced Algorithm for Determining Component Spectra Based on Principal Component Analysis," Appl. Spectr., vol. 39, pp. 610–614, 1985.

Kawata, S., K. Sasaki and S. Minami, "Component Analysis of Spatial and Spectral Patterns in Multispectral Images. I. Basis". J. Opt. Soc. Am. A., vol. 4, No. 11, pp. 2101–2106, 1987.

MacAulay, C, H. Tezcan and B. Palcic. "Adaptive Color Basis Transformation," Analyt. Quant. Cytol. Histol., vol. 11, No. 1, pp. 53–58, 1989.

McClelland, R.A., P. Finlay, K.J. Walker, D. Nicholson, J.F.R. Robertson, R.W. Blamey and R.I. Nicholson, "Automated Quantitation of Immunocytochemically Localized Estrogen Receptors in Human Breast Cancer," Cancer Res. vol. 50, pp. 3545–3550, 1990.

Ohta, N. "Estmating Absorption Bands of Component Dyes by Means of Principal Component Analysis," Analytical Chem., vol. 45, pp. 553–557, 1973.

Perez, F. and C.Koch, "Toward Color Image Sementation in Analog VLSI: Algorithm and Hardware," Int. J. Comp. Vision, vol. 12, pp. 17–42, 1994.

Sasaki, K., S. Kawata and S. Minami, "Estimation of Component Spectral Curves from Unknown Mixture Spectra," Appl. Optics, vol. 23, pp. 1955–1959, 1984.

Sasaki, K., S. Kawata and S. Minami, "Component Analysis of Spatial and Spectral Patterns in Multispectral Images. II. Entropy Minimization," J. Opt. Soc. Am. A., vol. 6, No. 1, pp. 73–79, 1989.

Sasaki, K., S. Kawata and S. Minami, "Constrained Non-linear Method for Estimating Component Spectra from Multicomponent Mixtures," Appl. Optics, vol. 22, pp. 3599–3603, 1983.

Schwartz, B.R., G. Pinkus, S. Bacus, M. Toder and D.S. Weinberg, "Cell Proliferation in Non–Hodgkin's Lymphomas," Am. J. Pathol., vol. 134, pp. 327–336, 1989.

Umbaugh, S.E. R.H. Moss, and W.V. Stoecker, "Automatic Color Segmentation of Images with Application to Detection of Variegated Coloring in Skin Tumors," IEEE Engr. Med. Biol. Magazine, Dec. 1989, pp. 43–52.

Yamamoto, S. and H. Yokouchi, "Automotive Recognition of Color Fundus Photographs," in *Digital Processing of Biomedical Images*, 1976.

Zhou, R., E.H. Hammond, W.T. Sause, P. Rubin, B. Emami, M.V. Pilepich, S.D. Asbell and D.L. Parker, "Quantitation of Prostate–Specific Acid Phosphate in Prostate Cancer: Reproducibility and Correlation with Subjective Grade," Modern Pathology, vol. 7, No. 4, pp. 440–448, 1994.

Zhou, R., D.L. Parker and E.H. Hammond, "Quantitative Peroxidase–Complex–Substrate Mass Determination in Tissue Sections by a Dual Wavelength Method," Analyt. Quant. Cytol. Histol., Vo. 14, No. 2, pp. 73–80, 1992.

R. Zhou, "Quantitive Evaluation of the Peroxidase–Antiperoxidase–Diaminobenzidine Stain in Double Stained Prostatic Tumor Slides by Dual Wavelength Technique," Master's Thesis, Department of Medical Informatics, University of Utah, Mar. 1992.

METHOD AND SYSTEM FOR MULTIPLE WAVELENGTH MICROSCOPY IMAGE ANALYSIS

MICROFICHE APPENDICES

A copy of the source code used in an example of the preferred embodiment of the invention is attached hereto as microfiche Appendix A which has 1 page and 31 frames and microfiche Appendix B which has 1 page and 44 frames. The code in Appendix A can be run on a PC-486DX running at 33 MHz. The code in Appendix B can be run on a SUN workstation. This source code represents one element of one preferred embodiment of the invention. It should be understood that the inventive concepts could be implemented in ways other than those shown in the microfiche appendix without departing from the inventive concept.

I. BACKGROUND OF THE INVENTION

A. Field of the Invention

This invention relates to the field of analysis of microscopy images. In particular, it relates to the analysis of microscopy images which are stained with several stains of different colors. Different colored stains are used to mark elements in the microscopically imaged material which have distinct structures and/or functions. Imaging of several stains simultaneously permits investigation of the interrelationship between different structural and functional elements. Moreover, automated imaging makes possible the quantification of the density of each stain, and hence of the corresponding stained element. The inventive method was developed particularly for the evaluation of histotogical and cytological specimens, but could also be used to evaluate structures in samples of non-biological materials.

B. The Background Art

The conventional approach for analyzing stained tissue is inspection of a section of the tissue under a microscope by a trained pathologist. However, it is difficult to obtain quantitative results with this method, and variability may exist between different observers, or between the same observer on different occasions. Therefore, methods for automated analysis of stained tissue sections is particularly desirable. Image analysis can provide quantitative information about the geometry (e.g., size and shape) of cells or other structures, density of staining, distribution of features within an image, etc.

Biochemical or immunocytochemical staining can be used to enhance the contrast of a structure or substance to which stain is attached. Measurement of stain density is relatively simple in a monochromic image. However, if several different stains are used, this determination is more difficult.

If the absorption bands of different stains do not overlap, the stains can be imaged independently by appropriate choice of narrow-band filters. This is known as the Exclusive Filtering Technique, and has been used by Bacus, et al. Am. J. Clin. Pathol. Vol. 90, pp. 223–239, 1988. This method, however, is dependent on the use of stains with non-overlapping absorption bands, and only a limited number of suitable stain combinations are available. This method can seldom be used with more than two stains simultaneously due to overlap of absorption bands.

Another approach is to use a color-space transformation model to separate stains, in images acquired with a three-channel color video camera. [e.g. Umbaugh et al., IEEE Engr. Med. Biol. Magazine, December 1989, pp. 43–52; MacAuley et al., Anal. and Quant. Cytol. and Histol. Vol. II, No. 1, pp. 53–58, 1989.]Three images are acquired (one red, one green, and one blue) after filtering of the image with broad-band filters. User-defined thresholds in color space are used to separate the different colored stains. However, this method has the drawbacks that spatial resolution is low, no more than three stains can be used, and the use of broad-band filters in the red, green and blue ranges may not be optimal for separating certain combinations of stains.

Principal component analysis has been suggested as a method for determining component spectral curves from the spectrum of a mixture of unknown components [Kawata et al., J. Opt. Soc. Am. A, Vol. 4, No. 11, pp. 2101–2106, 1987.]With this method, it is not necessary that spatial and spectral information about the components be known, but it is necessary to capture 13 images with 13 different narrow bandpass filters. This is the case even if only two components are being analyzed. The component spectrum is estimated with uncertainty, so quantitative analysis of a single component's spatial or spectral properties is not possible.

Prior art techniques may be satisfactory for two or possibly three stains, with certain restrictions on the absorption spectra of the stains. However, there is no method which reliably separates two or more stains with good spatial resolution and without limitations on the absorption spectra of the stains to be used. The present invention overcomes these limitations.

II. BRIEF SUMMARY AND OBJECTS OF THE INVENTION

The present invention is a method and system for performing analysis of multiply stained microscopy images. The preferred embodiment of the system includes a computer-controlled microscope and camera, software for controlling digitization and storage of images, and for decomposing multiply stained images to generate multiple single-stain images, and at least one computer on which said software is run. Several stains are used on the same sample so that the relationship between differently stained components can be seen. Color segmentation is performed to quantify the areas labelled with each stain. The color segmentation method used in the invention is based on differences of absorptivity spectra of stains (as measured at several different wavelengths) and can be used to decompose images including two, three or more stains.

The primary objectives of the present invention are:

1) to provide efficient separation of two or more different stains in a single sample.

2) to provide good spatial resolution of multiple single-stain images in multiply stained samples.

3) to provide a method for determining the optimum wavelengths for decomposing multiply stained images.

4) to provide a method and system for quantitative analysis of multiply stained images.

III. BRIEF DESCRIPTION OF THE DRAWINGS

IV. DETAILED DESCRIPTION OF THE PREFERRED EMBODIMENT

Theory of Operation

Figure 1:
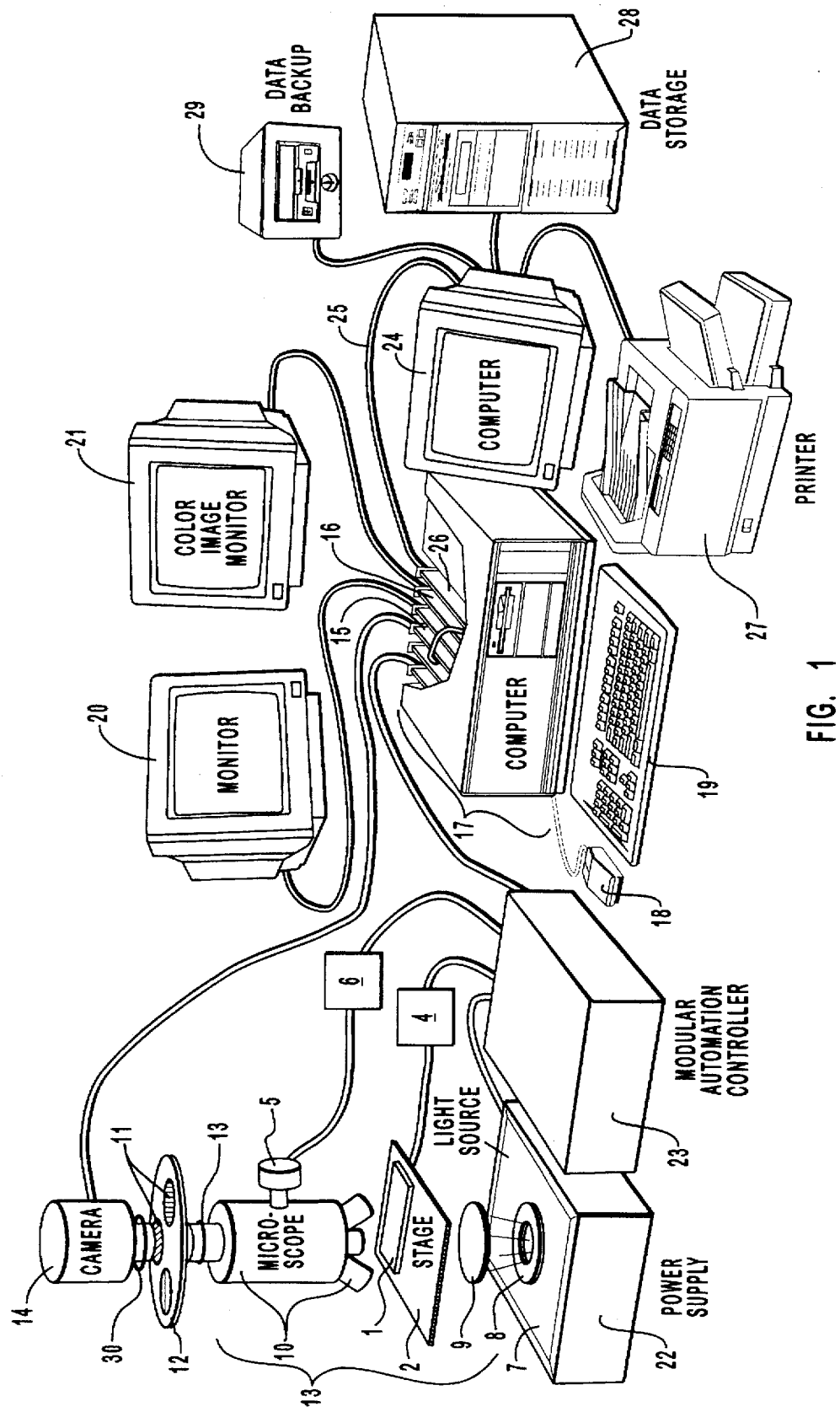
FIG. 1 is a diagram of equipment used in acquisition and processing of images of stained tissue sections.

The inventive method and system are based on the following theory. Let $G_k(x,y)$ be the light intensity at location x,y in the image formed by passing light of wavelength $\lambda k_k$ through a stained sample. Let $G0_k(x,y)$ be the light intensity at location x,y in the image formed by passing light through a region without stain. According to Beer's Law, $$G_k(x,y) = G0_k(x,y) e^{-\sum_{i=1}^{N} m_{ik} c_i(x,y) t_i(x,y)}$$  EQN. 1 where there are N stain components, $m_{ik}$ is the absorptivity of the ith stain component at wavelength $\lambda_k$, $c_i(x,y)$ is the concentration of the ith stain component at location (x,y), and $t_i(x,y)$ is the thickness of the ith stain component at location (x,y).

If $A_k$ is defined to be the absorbance of the sample at wavelength $\lambda_k$, and $\delta_i$, the mass density of stain component i, is defined as $c_i(x,y) \cdot t_i(x,y)$ then $$A_k(x,y) = \ln\left[\frac{G0_k(x,y)}{G_k(X,Y)}\right] = \sum_{i=1}^{N} m_{ik} \delta_i(x,y)$$  EQN. 2

If pairs of images (one with stain and one without stain) are acquired at N different wavelengths $\lambda_k(k=1 \ldots N)$, N linear equations of the following form are obtained:

$$A_k(x,y) = m_{1k}\delta_1(x,y) + m_{2k}\delta_2(x,y) + m_{3k}\delta_3(x,y) + \ldots + m_{ik}\delta_i(x,y) + \ldots + m_{Nk}\delta_N(x,y)$$  EQN. 3

If matrices A, D, and M are defined as:

$$A = \begin{bmatrix} A_1(x,y) \\ A_2(x,y) \\ \vdots \\ A_k(x,y) \\ \vdots \\ A_N(x,y) \end{bmatrix} \quad D = \begin{bmatrix} \delta_1(x,y) \\ \delta_2(x,y) \\ \vdots \\ \delta_i(x,y) \\ \vdots \\ \delta_N(x,y) \end{bmatrix}$$  EQN. 4

$$M = \begin{bmatrix} m_{11} & m_{21} & \ldots & m_{i1} & \ldots & m_{N1} \\ m_{12} & m_{22} & \ldots & m_{i2} & \ldots & m_{N2} \\ \vdots & & & & & \vdots \\ m_{1k} & m_{2k} & \ldots & m_{ik} & \ldots & m_{Nk} \\ \vdots & & & & & \vdots \\ m_{1N} & m_{2N} & \ldots & m_{iN} & \ldots & m_{NN} \end{bmatrix}$$

then the N linear equations can be written in the form $$A = M \cdot D$$

It should be noted that indices for array elements are given in the form (column, row). That is, $m_{ik}$ is in row k and column i. If $|M| \neq 0$, then $$\delta_i(x,y) = \frac{\Delta_i(x,y)}{|M|}$$  EQN. 5 for i=1 ... N, where $$\Delta_1(x,y) = \begin{vmatrix} A_1(x,y) & m_{21} & \ldots & M_{i1} & \ldots & m_{N1} \\ A_2(x,y) & m_{22} & \ldots & m_{i2} & \ldots & m_{N2} \\ \vdots & & & & & \vdots \\ A_N(x,y) & m_{2N} & \ldots & m_{iN} & \ldots & m_{NN} \end{vmatrix}$$  EQN. 6A $$\Delta_2(x,y) = \begin{vmatrix} m_{11} & A_1(x,y) & m_{31} & \ldots & m_{i1} & \ldots & m_{N1} \\ m_{12} & A_2(x,y) & m_{32} & \ldots & m_{i2} & \ldots & m_{N2} \\ \vdots & & & & & & \vdots \\ m_{1N} & A_N(x,y) & m_{3N} & \ldots & m_{iN} & \ldots & m_{NN} \end{vmatrix}$$  EQN. 6B $$\Delta_i(x,y) = \begin{vmatrix} m_{11} & m_{21} & \ldots & m_{(i-1)1} & A_1(x,y) & m_{(i-1)1} & \ldots & m_{N1} \\ m_{12} & m_{22} & \ldots & m_{(i-1)2} & A_2(x,y) & m_{(i+1)2} & \ldots & m_{N2} \\ \vdots & & & & & & & \vdots \\ m_{1k} & m_{2k} & \ldots & m_{(i-1)k} & A_k(x,y) & m_{(i+1)k} & \ldots & m_{Nk} \\ \vdots & & & & & & & \vdots \\ m_{1N} & m_{2N} & \ldots & m_{(i-1)N} & A_N(x,y) & m_{(i+1)N} & \ldots & m_{NN} \end{vmatrix}$$  EQN. 6C and so forth.

The densities of the N different stain components can be determined from EQN. 5 if the N absorbance images $A_k$ and N×N absorptivity values $m_{ik}$ (i=1 ... N, k=1 ... N) are available. According to Equation 2, the N absorbance images $A_k$ can be obtained from N image pairs $G_k$ and $G0_k$ measured at the N different wavelengths. The absorptivity values, $m_{ik}$, are more difficult to determine because the absorption spectrum of a stain in a tissue sample is usually different from the absorption spectrum of the stain in solution. Furthermore, the amount of stain in a given tissue sample is unknown. Thus it is not feasible to use an equation which requires knowledge of absorptivity values to determine mass densities of stains in tissue.

In the present invention, the problem of unknown absorptivities is solved by selecting a wavelength $\lambda_N$ at which the absorptivity $m_{iN}$ is non-zero for each stain component and defining the following ratio matrices:

$$R = \begin{vmatrix} \frac{m_{11}}{m_{1N}} & \frac{m_{21}}{m_{2N}} & \cdots & \frac{m_{i1}}{m_{iN}} & \cdots & \frac{m_{N1}}{m_{NN}} \\ \frac{m_{12}}{m_{1N}} & \frac{m_{22}}{m_{2N}} & \cdots & \frac{m_{i2}}{m_{iN}} & \cdots & \frac{m_{N2}}{m_{NN}} \\ \vdots & & & & & \vdots \\ \frac{m_{1k}}{m_{1N}} & \frac{m_{2k}}{m_{2N}} & \cdots & \frac{m_{ik}}{m_{iN}} & \cdots & \frac{m_{Nk}}{m_{NN}} \\ \vdots & & & & & \vdots \\ \frac{m_{1(N-1)}}{m_{1N}} & \frac{m_{2(N-1)}}{m_{2N}} & \cdots & \frac{m_{i(N-1)}}{m_{iN}} & \cdots & \frac{m_{N(N-1)}}{m_{NN}} \\ \frac{m_{1N}}{m_{1N}} & \frac{m_{2N}}{m_{2N}} & \cdots & \frac{m_{iN}}{m_{iN}} & \cdots & \frac{m_{NN}}{m_{NN}} \end{vmatrix}$$

EQN. 7

$$= \begin{vmatrix} r_{11} & r_{21} & \cdots & r_{i1} & \cdots & r_{N1} \\ r_{12} & r_{22} & \cdots & r_{i2} & \cdots & r_{N2} \\ \vdots & & & & & \vdots \\ r_{1k} & r_{2k} & \cdots & r_{ik} & \cdots & r_{Nk} \\ \vdots & & & & & \vdots \\ r_{1(N-1)} & r_{2(N-1)} & \cdots & r_{i(N-1)} & \cdots & r_{N(N-1)} \\ 1 & 1 & \cdots & 1 & \cdots & 1 \end{vmatrix}$$

$\Pi_1(x,y) =$ EQN. 8A $$\begin{vmatrix} A_1(x,y) & r_{21} & \cdots & r_{i1} & \cdots & r_{N1} \\ A_2(x,y) & r_{22} & \cdots & r_{i2} & \cdots & r_{N2} \\ \vdots & & & & & \vdots \\ A_k(x,y) & r_{2k} & \cdots & r_{ik} & \cdots & r_{Nk} \\ \vdots & & & & & \vdots \\ A_{N-1}(x,y) & r_{2(N-1)} & \cdots & r_{i(N-1)} & \cdots & r_{N(N-1)} \\ A_N(x,y) & 1 & \cdots & 1 & \cdots & 1 \end{vmatrix}$$

$\Pi_2(x,y) =$ EQN. 8B $$\begin{vmatrix} r_{11} & A_1 & r_{31} & \cdots & r_{i1} & \cdots & r_{N1} \\ r_{12} & A_2 & r_{32} & \cdots & r_{i2} & \cdots & r_{N2} \\ \vdots & & & & & & \vdots \\ r_{1k} & A_k & r_{3k} & \cdots & r_{ik} & \cdots & r_{Nk} \\ \vdots & & & & & & \vdots \\ r_{1(N-1)} & A_{N-1} & r_{3(N-1)} & \cdots & r_{i(N-1)} & \cdots & r_{N(N-1)} \\ 1 & A_N & 1 & \cdots & 1 & \cdots & 1 \end{vmatrix}$$

-continued $\Pi_i(x,y) =$ EQN. 8C $$\begin{vmatrix} r_{11} & \cdots & r_{(i-1)1} & A_1(x,y) & r_{(i+1)1} & \cdots & r_{N1} \\ r_{12} & \cdots & r_{(i-1)2} & A_2(x,y) & r_{(i+1)2} & \cdots & r_{N2} \\ \vdots & & & & & & \vdots \\ r_{1k} & \cdots & r_{(i-1)k} & A_k(x,y) & r_{(i+1)k} & \cdots & r_{Nk} \\ \vdots & & & & & & \vdots \\ r_{1(N-1)} & \cdots & r_{(i-1)(N-1)} & A_{N-1}(x,y) & r_{(i+1)(N-1)} & \cdots & r_{N(N-1)} \\ 1 & \cdots & 1 & A_N(x,y) & 1 & \cdots & 1 \end{vmatrix}$$

$\Pi_N(x,y) =$ EQN. 8D $$\begin{vmatrix} r_{11} & \cdots & r_{i1} & \cdots & r_{(N-1)1} & A_1(x,y) \\ r_{12} & \cdots & r_{i2} & \cdots & r_{(N-1)2} & A_2(x,y) \\ \vdots & & & & & \vdots \\ r_{1k} & \cdots & r_{ik} & \cdots & r_{(N-1)k} & A_k(x,y) \\ \vdots & & & & & \vdots \\ r_{1(N-1)} & \cdots & r_{i(N-1)} & \cdots & r_{(N-1)(N-1)} & A_{N-1}(x,y) \\ 1 & \cdots & 1 & \cdots & 1 & A_N(x,y) \end{vmatrix}$$

and so on. Then the mass density of the ith stain component at location x,y can be calculated (by modifying EQN. 5) as:

$$\delta_i(x,y) = \frac{\Pi_i(x,y)}{m_{iN}R} \quad (R \neq 0, m_{iN} \neq 0)$$

EQN. 9 where R is as defined in EQN. 7. The absorbance values $A_k$ found in matrices $\Pi_i$ can be calculated readily from measured values, as described in EQN. 2. The absorptivity ratio values found in matrices $\Pi_i$ and R can be calculated from absorbance values measured from singly stained samples, as follows:

$$\frac{m_{i1}}{m_{i2}} = \frac{m_{i1}\delta_i}{m_{i2}\delta_i} = \frac{A_1}{A_2}$$

EQN. 10 where $A_1$ and $A_2$ are measured at wavelengths $\lambda_1$ and $\lambda_2$, respectively. $\delta_i$ is constant for a particular stain at a particular location, so it cancels out. The absorptivity value $m_{iN}$ used in equation 9 simply indicates the relative absorbances of the different stains and acts as a constant scaling factor for the intensity of pixels within a particular image. Therefore, it is not necessary to have an exact measurement of $m_{iN}$ in order to perform color image segmentation.

Based on the theory outlined above, in the inventive method and system, a mass density value is calculated for each stain at each field of the slide. EQN. 9 is used, substituting in absorptivity ratios calculated from single-stain absorbance values (EQN. 10) and absorbance values measured in multiple-stained samples at each wavelength (EQN. 2). It is then possible to generate a separate mass-density image for each stain. The procedure for determining mass density is described more specifically in connection with the examples presented subsequently.

Optimization of Wavelengths for Image Segmentation

Although the inventive method can be carried out with any wavelengths at which the absorptivity ratios of the stain components are different, it is preferable to select wavelengths that minimize error in the image measurement and segmentation. Optimization of wavelengths increases the accuracy and resolution of color image segmentation.

Two wavelength-dependent parameters should be minimized. One is the variance of the mass density estimate. The other is the chromatic aberration in the optical path of the imaging system. The chromatic aberration in the optical path of the imaging system can be determined from the shift in the images obtained at different wavelengths. For example, image shift can be measured conveniently from images of a cross hair stage micrometer.

In order to choose the wavelengths at which variance of the mass density estimate is minimal, the spectral properties of the stain components must be known. The absorption spectra of stains can be estimated from singly-labelled slides with the use of a microphotometer. A microphotometer with intervals of 10 nm or less is suitable for measuring absorption spectra.

As shown in EQN. 5, mass density is a function of absorbance and absorptivity. Since the absorptivity $m_{ik}$ is constant for a specific stain i at a specific wavelength $\lambda_k$, we can assume that $\delta_i$ is simply a function of absorbance, i.e. $f_i(A_1, A_2, \ldots, A_N)$. $f_i(A_1, A_2, \ldots A_N)$ can be represented as a Taylor series:

$$\delta_i = f_i(A_1, A_2, \ldots, A_N) = f_i(A_{10}, A_{20}, \ldots, A_{N0}) + \qquad \text{EQN. 11}$$

$$\sum_{k=1}^{N} (A_k - A_{k0}) \frac{\partial f_i(A_{10}, A_{20}, \ldots, A_{N0})}{\partial A_k} + \ldots +$$

$$\frac{1}{n!} \sum_{k=1}^{N} (A_k - A_{k0})^n \frac{\partial^n f_i(A_{10}, A_{20}, \ldots, A_{N0})}{\partial^n A_k} + \ldots$$

where $A_{k0}$ is the mean absorbance at $\lambda_k$. Assuming that higher order terms approach zero, using only the first terms of the series gives a good approximation:

$$\delta_i = f_i(A_1, A_2, \ldots, A_N) \approx f_i(A_{10}, A_{20}, \ldots, A_{N0}) + \qquad \text{EQN. 12}$$

$$\sum_{k=1}^{N} (A_k - A_{k0}) \frac{\partial f_i(A_{10}, A_{20}, \ldots, A_{N0})}{\partial A_k}$$

The variance of $\delta_i$ can be represented by the expected value of the square of the difference between $f_i(A_1, A_2, \ldots, A_N)$ and the mean value of the function, $f_i(A_{10}, A_{20}, \ldots, A_{N0})$:

$$\sigma_{\delta_i}^2(\lambda_1, \lambda_2, \ldots, \lambda_N) = E\{[f_i(A_1, A_2, \ldots, A_N) - f_i(A_{10}, A_{20}, \ldots, A_{N0})]^2\} \qquad \text{EQN. 13}$$

By substituting EQN. 12 into EQN. 13, and assuming the $A_k$s are independent, the following equation is obtained:

$$\sigma_{\delta_i}^2(\lambda_1, \lambda_2, \ldots, \lambda_N) = \qquad \text{EQN. 14}$$

$$\sum_{k=1}^{N} E\left\{ \left[ (A_k - A_{k0}) \frac{\partial f_i(A_{10}, A_{20}, \ldots, A_{N0})}{\partial A_k} \right]^2 \right\}$$

Since the partial derivative of $f_i(A_{10}, A_{20}, \ldots, A_{N0})$ with respect to $A_k$ does not vary as a function of $\lambda_k$, the variance of $\delta_i$ can be obtained from the variances of the $A_k$s:

$$\sigma_{\delta_i}^2(\lambda_1, \lambda_2, \ldots, \lambda_n) = \qquad \text{EQN. 15}$$

$$\sum_{k=1}^{N} \left[ \frac{\partial f_i(A_{10}, A_{20}, \ldots, A_{N0})}{\partial A_k} \right]^2 \sigma^2(A_k) \quad (k=1, 2, \ldots, N)$$

If the absorption spectra of the stain components are known, the variance of $\delta_i$ can be obtained for each stain component i by using equation 15. The optimum wavelengths for multiple wavelength segmentation of a particular combination of stains is determined by minimizing the sum of the variances.

Practice of the Invention

The practice of the invention requires that samples of interest be prepared, and that images be acquired and analyzed. Image acquisition requires the use of suitable hardware and software; image analysis is performed by software which implements the equations which have been described previously to determine mass density images for each stain component. Sample preparation, equipment, and software configuration will now be described. Finally, two examples showing the use of the invention for performing segmentation of dual- and triple-stained images will be provided.

Preparation of Samples

In the application of the invention to the analysis of biological tissue, the preferred approach is to prepare slides from thin (e.g., 4 μm) sections of tissue. Sections can be of any thickness which allows the microscope to be focussed clearly on the tissue. The tissue is fixed and dehydrated, stained, and cover-slipped. Certain non-biological materials may not need to be fixed and dehydrated, and if components of interest are naturally colored, staining may not be necessary. Moreover, materials which are sufficiently rigid do not need to be mounted on slides. Various stains known in the prior art can be used in the practice of the invention. The choice of stain will depend on the structures of interest in the tissue to be stained. Many suitable combinations of stains can be found.

Examples of some stains which may be used in the practice of the invention are:

1) hematoxylin—a blue stain which stains nuclei of cells
2) FastRed—a pink stain which stains the cytoplasm of cells
3) PAP-DAB—a brown stain which can be used to immunocytochemically label various structures against which antibodies have been produced.
4) Feulgen—stains DNA in cell
5) FastGreen and NEC chromagen—used for immunohistological staining The above stains are intended to serve only as examples, and the practice of the invention is not limited to the use of these stains.

In the practice of the invention, in order to decompose images labelled with several different stains it is necessary to prepare a number of control slides along with the multiply-stained sample slides. One singly-stained control slide must be prepared with each different stain. In addition, at least one unstained control slide must be prepared (which will be used to determine the amount of attenuation caused by the tissue section alone). Sample and control slides should be taken from serial sections of the tissue of interest and treated identically except for the differences in staining procedure.

Equipment

The equipment used in the preferred embodiment of the invention is depicted in FIG. 1. Slide 1, which contains a sample to be imaged, is secured to stage 2 of microscope 3. Microscope 3 preferably has a repeatable focus level and a chromatic aberration-free objective. Stage 2 is an XY translation stage driven by an XY stepper motor 4 (max speed 30,000 µm/sec; resolution 0.1 µm; reproducibility 4 µm; accuracy 3 µm). The position of the stage in the Z-direction is adjusted with focus knob 5. Z-axis stepper motor 6 is used to control focus knob 5 in the preferred embodiment of the invention (stepper motor resolution is 0.01 µm, maximum speed is 27,000 µm/sec). Light from light source 7 passes through field iris 8 and condenser 9. After passing through slide 1, said light passes through microscope observation tube 10 and through a filter 11 carried in filter wheel 12. Filter wheel 12 contains a number of filters which are preferably chromatic aberration-free narrow bandpass filters. Light Source 7 is preferably a conventional light source. In an alternate embodiment of the invention, a fluorescent light source may be placed above the sample and the light emitted from slide 1 will travel through microscope observation tube 10 and filter 11. The system must also include sensors for the incident and the emitted light. In the embodiment of the invention depicted here, microscope observation tube 10 is a conventional microscope observation tube which has been modified so that filter wheel 12 can be attached between photo eyepiece 13 and camera 14. Camera 14 is a high-resolution digital CCD camera (in the preferred embodiment of the invention, a XILLIX 1400 is used), which is attached to the top of microscope observation tube 10. Camera 14 is controlled by signals sent from camera control card 15. Camera 14 is used to acquire and digitize microscopic images. These images are subsequently displayed on color monitor 21 by a pseudo color image display board (UNIVISION 2600) 16. Both camera control card 15 and image display board 16 are installed in computer 17. In the presently preferred embodiment of the invention, computer 17 is a PC-486DX running at 33 MHz or comparable computer. Computer 17 is preferably equipped with a mouse 18, a keyboard 19, and an SVGA monitor 20. Text generated by the software (instructions, data, etc.) is displayed on monitor 20. Images from image display board 16 are displayed on color image monitor 21, which is preferably a 1280×1024 high resolution monitor. Light source 7 is powered by power supply 22. Light source 7 is modified so that it will operate when power supply 22 is either a conventional AC power supply or a DC stabilized power supply. In the preferred embodiment of the invention, power supply 22 is a DC power supply which may be computer controlled. Power supply 22, Z-axis stepper motor 6, stage 2, shutter 30 of camera 14, and filter wheel 12 are computer controlled in the preferred embodiment of the invention. Stage 2, power supply 22, and filter wheel 12 are controlled by modular automation controller 23 (for example, a MAC-2000 Modular Automation Controller), which is in turn controlled by signals sent over a communication line from computer 17. In the preferred embodiment, said communication line is an RS232 line, but depending on the particular computer and controller used, it may be equally or more preferable to use another communication line. In an alternate, less preferred embodiment of the invention, power supply 22 is controlled manually, and XYZ motion of stage 2 is controlled by a manually operated joystick.

In the presently preferred embodiment of the invention, computer 17 is connected to a second computer 24, which is preferably a SUN workstation, via an ETHERNET network 25 or comparable network. A network card 26 is installed in computer 17 (an EtherCard Plus16 in the preferred embodiment of the invention) to control the transfer of data over the network. Alternatively, the invention could be carried out on a single computer, providing said computer was capable of running all required image acquisition, storage, and analysis software. The invention is not limited to the use of a particular computer system or systems. Image data acquired with computer 17 is transferred to second computer 24 for storage and analysis. Computer 24 is preferably attached to a printer 27 on which data and images can be printed out, data storage device 28, which stores data prior to and during processing and which is preferably a hard disk, and a data backup device 29, which is a tape driver in the preferred embodiment of the invention. Various devices may be used for short- and long-term data storage and for generation of hard copies of data and images, and the devices described herein are intended only to serve as examples.

Software

In the preferred embodiment of the invention, computer 17 is a 486DX PC running DOS 5.0 and Microsoft Windows 3.1. The software running on computer 17 controls operation of the microscope, digitization of microscope images, and archival and retrieval of images. All of the above software was developed using the basic image processing function package OPTIMAS 4.10. This function package allows C subroutines to be linked in with OPTIMAS functions. Computer 24 is a SUN workstation running the UNIX operating system. The software running on computer 24 comprises batch mode image processing software written in the C programming language.

The practice of the invention is not limited to a particular computer system, software package or programming language. It would be possible for one skilled in the art of software development and computer control to implement the invention on various types of computers and in various programming languages. Moreover, some or all of the functions carried out by software could be controlled by hardware, instead (e.g., matrix operations could be carried out by a digital signal processing chip). It would also be possible to use programmable chips in place of software.

The inventive method is largely computer controlled. In the preferred embodiment of the invention, image acquisition is performed in an automated manner. However, in an alternative embodiment of the invention, image acquisition can be performed manually. Both approaches are described below.

Manual Image Acquisition

When the "manual" image acquisition procedure is used, adjustment of the microscope (i.e. imaged field, focus, light intensity, etc.) is made by hand, by a user. The digitization and subsequent storage and analysis of digitized images is performed under software control. When image acquisition is done manually, a reference image must be acquired before each test image is acquired, since manually set light intensities may vary. Accordingly, if two wavelengths are used, 4M images must be obtained if each slide has M fields which must be imaged (i.e., at each field, one reference image and one test image must be obtained at each wavelength). If three wavelengths are used, 6M images must be obtained (i.e., at each field, one reference image and one test image at each wavelength). The steps for manual image acquisition in the two-wavelength case are shown in Table 1. Although the manual image acquisition procedure can be expanded for cases where three or more wavelengths are used, this method is unwieldy for larger numbers of wavelengths, and it is preferred that the automated image acquisition procedure be used.

TABLE 1
Manual dual wavelength image acquisition
(1) m=1;
(2) Manually move to a clear region (without any tissue or stain);
(3) Manually switch to filter $f_a$ and adjust the illumination to an appropriate level;
(4) Capture a reference image $G_{ao}[m]$ and save it directly on disk 26;
(5) Manually move to the tissue structure of interest;
(6) Capture tissue image $G_a[m]$ and save it on disk 26;
(7) Manually change to filter $f_b$ and adjust the illumination to an appropriate level;
(8) Capture tissue image $G_b[m]$ and save it on disk 26;
(9) Manually move to the clear region;
(10) Capture reference image $G_{bo}[m]$ and save it on disk 26;
(11) Set m=m+1 and Goto step (2) until m=M, which is the number of microscopic fields in a slide.

Automated Image Acquisition

In "automated" image acquisition, control of the microscope (imaged field, focus, light intensity, etc.) is carried out with software. Digitization, storage and analysis of digitized images is also under software control. When image acquisition is automated, only one reference image must be obtained before all M fields are imaged. A rectangular area containing the fields of interest is defined by the user before image acquisition is begun. The light intensities used at each wavelength are set beforehand. Light intensities are set automatically during image acquisition and therefore are less variable. If two wavelengths are used, 2M+2 images must be obtained if each slide has M fields (i.e., one reference image at each wavelength, and one sample image at each field and each wavelength). Steps performed in dual-wavelength automated image acquisition are listed in Table 2.

If three wavelengths are used, 3M+3 images must be obtained (i.e., one reference image at each wavelength and at each field, one sample image at each wavelength). Steps performed in triple-wavelength automated image acquisition are listed in Table 3.

The automated image acquisition procedure can readily be expanded for use with more than three wavelengths. In general, reference images are acquired at each wavelength from a clear region of the slide, and then tissue images are acquired at each wavelength, from each field within the area of interest of the slide. If N wavelengths are used, N×M+N or N(M+1) images, must be obtained. It is clear that as N increases, the image acquisition process becomes increasingly time consuming and would be virtually impossible to perform manually.

TABLE 2
Automatic dual wavelength image acquisition
(1) m=1;
(2) Manually move the stage and focus on a clear region without tissue or stain under software prompt—software records the position for automatic scan;
(3) Manually move the stage and focus on the tissue structure of interest under software prompt—software records the position for further automatic scan;
(4) Move stage and focus on the region without tissue or stain (this and subsequent steps are under software control);
(5) Change to filter $f_a$ and set illuminating intensity to $I_a$;
(6) Capture reference image $G_{ao}$ and save directly on a disk 26;
(7) Change to filter $f_b$ and set illuminating intensity to $I_b$;
(8) Capture reference image $G_{bo}$ and save directly on a disk 26;
(9) Move stage to the tissue structure of interest;
(10) Change to filter $f_a$ and reset illuminating intensity to $I_a$;
(11) Capture tissue image $G_a$ and save directly on a disk 26;
(12) Change to filter $f_b$ and reset illuminating intensity to $I_b$;
(13) Capture tissue image $G_b$ and save directly on a disk 26;
(14) Set m=m+1 and Goto step (9) until m=M microscopic fields have been imaged in a defined rectangular area.

TABLE 3
Automatic triple wavelength image acquisition
(1) m=1;
(2) Manually move the stage and focus on a clear region under software prompt—software records the position for further automatic scan;
(3) Manually move the stage and focus on tissue structure of interest under software prompt—software records the position for further automatic scan;
(4) Automatically change to filter $f_a$ and set illuminating intensity to $I_a$ (this and subsequent steps are controlled by software running on PC);
(5) Capture reference image $G_{ao}$ and save the image directly to a disk 26;
(6) Change to filter $f_b$ and set illuminating intensity to $I_b$;
(7) Capture reference image $G_{bo}$ and save the image directly to disk 26;
(8) Change to filter $f_c$ and set illuminating intensity to I3;
(9) Capture reference image $G_{co}$ and save the image directly to disk 26;
(10) Move stage and focus on tissue structure of interest;
(11) Capture tissue image $G_c$ and save the image directly to disk 26;
(12) Change to filter $f_b$ and reset illuminating intensity to $I_b$;
(13) Capture tissue image $G_b$ and save the image directly to disk 26;
(14) Change to filter $f_a$ and reset illuminating intensity to $I_a$;
(15) Capture tissue image $G_a$ and save the image directly to disk 26;
(16) Change to filter $f_c$ and reset illuminating intensity to $I_c$;
(17) Set m=m+1 and Goto step (10) until m=M microscopic fields have been imaged in the user defined area;

Image Data Acquisition and Processing

Figure 2:
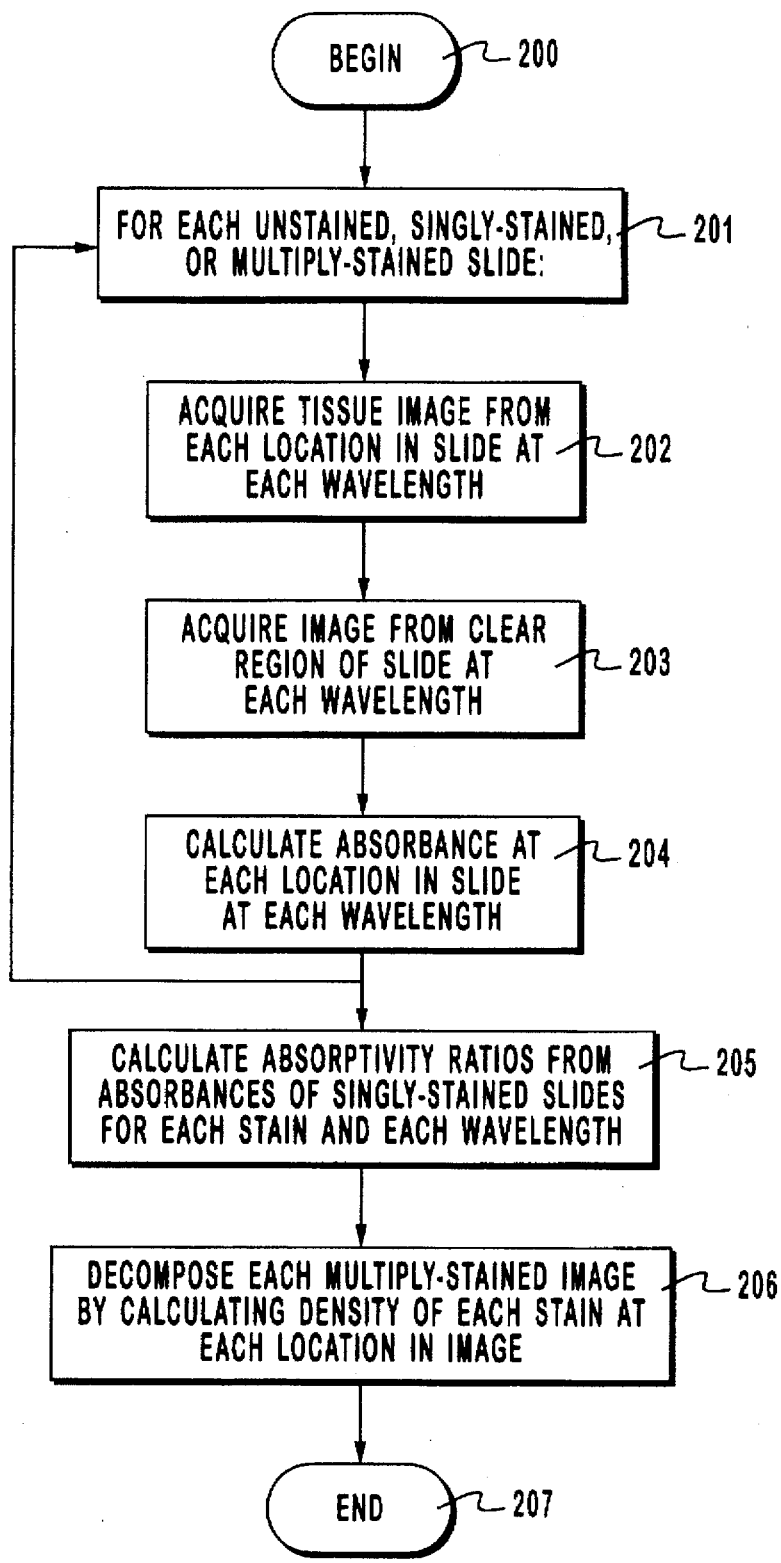
FIG. 2 is a flow chart diagram outlining the major steps in data acquisition and analysis.

The overall procedure used for image data acquisition and processing is shown in FIG. 2. For each slide (indexing is performed at step 201), a tissue image is acquired from each stained field of the tissue sample, at each wavelength of interest (step 202). In step 203, images are acquired from a clear region of the slide (i.e. a region where no tissue is present), at each wavelength. The absorbance is then calculated at each location and at each wavelength (step 204). Steps 202 through 204 are repeated for each slide, as indicated at step 201. After all images have been acquired, absorptivity ratios are calculated from the absorbances of slides stained with single stains, at each wavelength (step 205), and multiply-stained images are decomposed making use of the previously calculated absorbance and absorptivity ratios (step 206).

Figure 3:
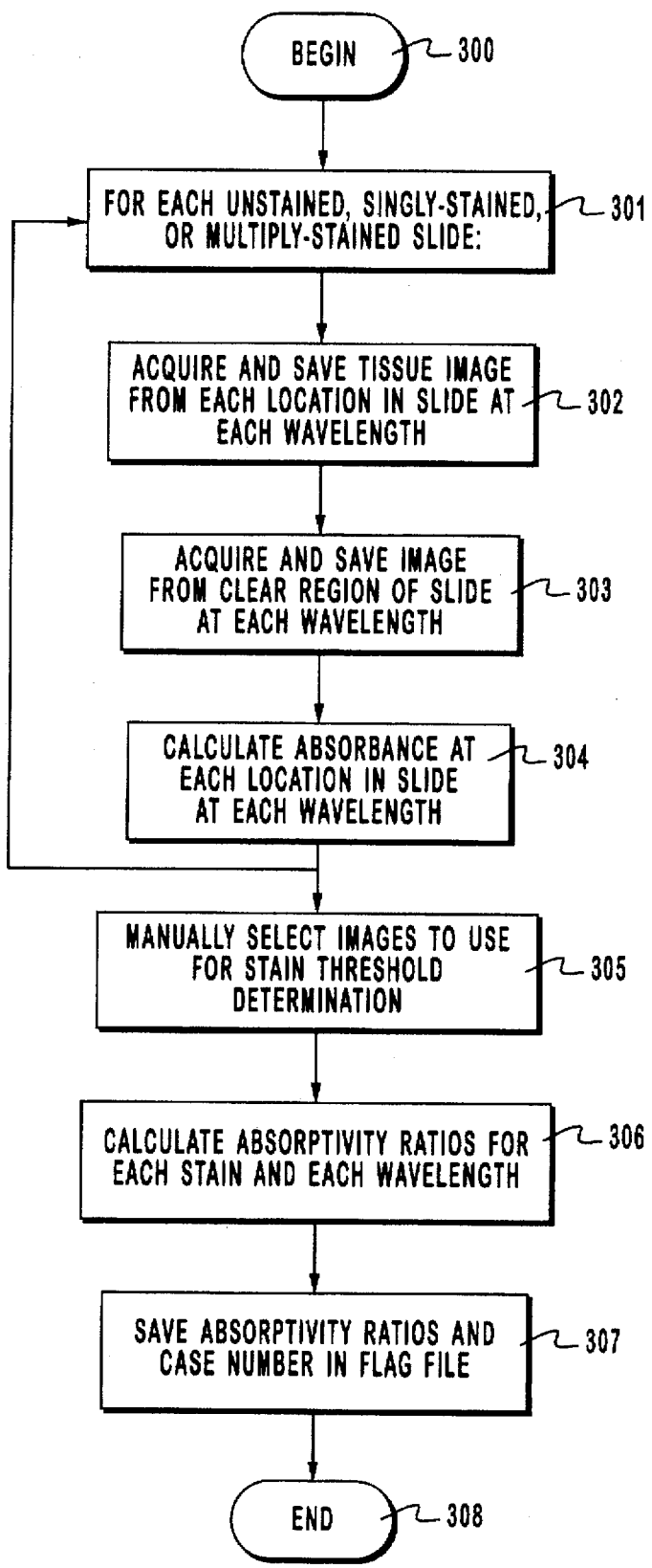
FIG. 3 is a flow chart diagram of the image acquisition procedure.

In the example of the preferred embodiment of the invention depicted in FIG. 1, the procedure shown in FIG. 2 is carried out on two different computers. The software which carries out the image acquisition steps is run on computer 17, which is a PC in the presently preferred embodiment of the invention, while the image decomposition steps are carried out on computer 24. The software run on computer 17 in this example of the presently preferred embodiment is listed in microfiche Appendix A. The image acquisition steps are shown in FIG. 3. In step 302, images are acquired from stained field of the tissue sample, at each wavelength of interest, and saved. In step 303, images are acquired from a clear region of the slide (i.e. a region where no tissue is present), at each wavelength and saved. Either the manual procedure or automated procedure described above may be used to acquire images. The image data is stored directly on the data storage device 28 of computer 24. Image data is preferably stored immediately after it is acquired; it would also be possible to store a large block of image data in one step after image acquisition is completed. In the presently preferred embodiment of the invention, computer 24 is a SUN workstation, and data storage device 28 on the SUN system is transparent to the computer 17 (the PC). Data can thus be written to data storage device 28 using the same commands which can be used to write to disks of the PC. Images from which staining thresholds can be calculated are determined manually (stept 305). Absorptivity ratios are calculated (step 306), and in step 307, absorptivity ratios and the case number are stored in a "flag file" on data storage device 28 of computer 24.

Batch Mode image Analysis

Figure 4:
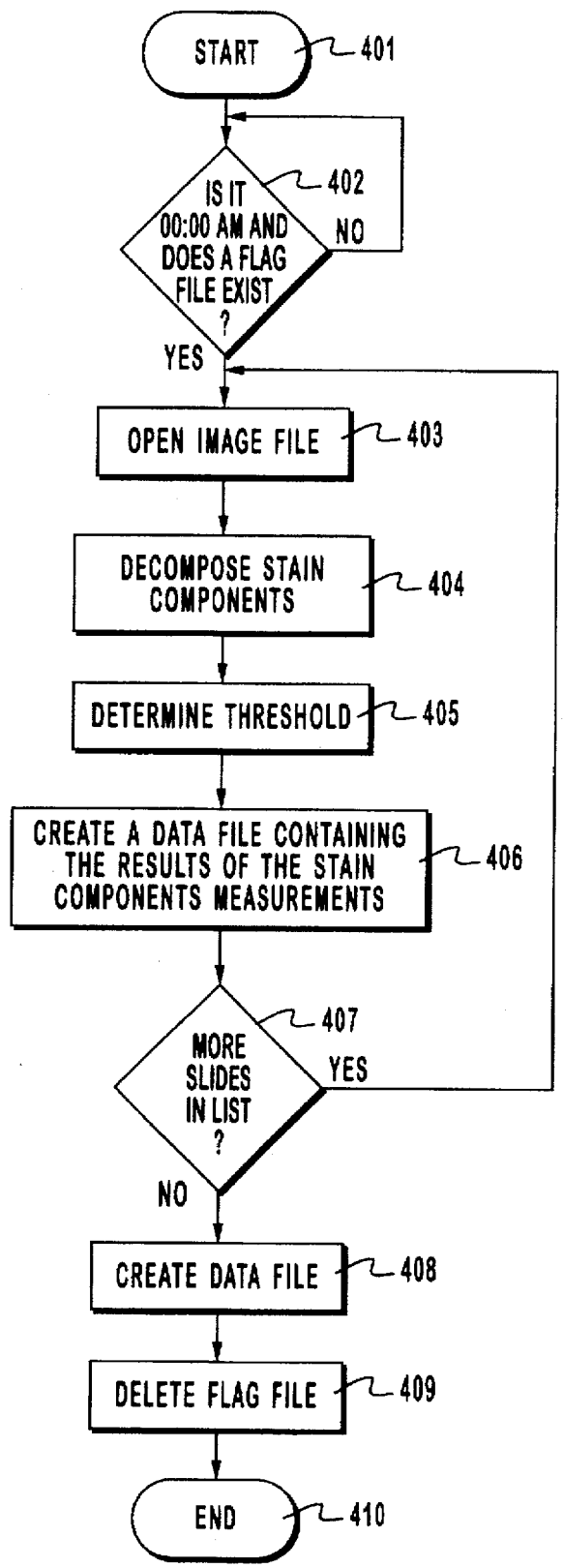
FIG. 4 is a flow chart diagram of the batch processing procedure.

Because image analysis is time-consuming, it is desirable that if many images are to be analyzed, this analysis be carried out at a time when the use of the computer for other tasks is not needed, e.g. in the middle of the night. It is also preferable that multiple images be processed without the need for user intervention. The batch mode image analysis procedure makes it possible to process a large amount of image data without user intervention. This procedure is carried out by a computer program running on computer 24. The software run on computer 24 in this example of the presently preferred embodiment is listed in microfiche Appendix B. The procedure for batch mode image analysis is shown in FIG. 4. The batch mode procedure is started at step 401. In step 402, the program checks for the presence of a flag file on data storage device 28. The flag file is created and stored on data storage device 28 subsequent to the storage of image files on data storage device 28, as shown in FIG. 3. Accordingly, the presence of a flag file indicates that image files are also present on the disk. In step 402, the system time is also evaluated; the program waits until the desired starting time is reached. The starting time shown in FIG. 4. is 00:00 a.m. (midnight), but any time which is convenient can be used in the practice of the invention. When the starting time is reached, the first image file listed in the flag file is opened (step 403). For each image, the stain components are decomposed (step 404) and the threshold stain density is determined for each component image (step 405). The threshold stain density has a value which is higher than the density of the background stain, but below the stain density of positively stained tissue. Finally, a data file containing the results of the stain component measurements is created (step 406). If additional files are listed in the flag file, as determined in step 407, steps 403 through 406 are repeated for each file, until all files listed in the flag file have been processed. A data file containing the parameters related to each stain component (e.g. stain intensity and extent) is then created (step 408). The flag file is deleted from data storage device 28 (step 409), and the batch procedure is ended (step 410).

The following examples illustrate the use of the invention in the segmentation of dual—and triple-stained images. In each example, the method was used to analyze images of prostate cancer tissue specimens.

EXAMPLE 1

Dual-wavelength segmentation of dual-stained image.

In this example, sample slides labelled with two stains were analyzed. PAP-DAB was used to stain Prostate Specific Acid Phosphatase (Stain 1) in the cytoplasm, and hematoxylin (Stain 2) was used to stain cell nuclei. Slides were prepared with 1) both PAP-DAB+hematoxylin, 2) PAP-DAB alone, 3) hematoxylin alone, or 4) no stain. Only one slide each was prepared with the single stains or no stain, while a set of slides were prepared with both stains. All slides were processed together to insure identical staining with each particular stain. The absorbances measured at wavelengths $\lambda_a$ and $\lambda_b$ were:

$$A(x,y) = \ln\left[\frac{G0_a(x,y)}{G_a(x,y)}\right] \quad B(x,y) = \ln\left[\frac{G0_b(x,y)}{G_b(x,y)}\right] \quad \text{EQN. 16}$$

respectively. $G0_a$ and $G0_b$ were measured in regions without tissue and stain. From EQN. 9, the mass densities of stain 1 and stain 2 were found to be:

$$\delta_1(x,y) = \frac{A(x,y) - \beta \cdot B(x,y)}{\hat{m}_{1b} \cdot (\alpha - \beta)} \quad \text{EQN. 17}$$

$$\delta_2(x,y) = \frac{\alpha \cdot B(x,y) - A(x,y)}{\hat{m}_{2b} \cdot (\alpha - \beta)}$$

$$(\alpha \neq \beta, \hat{m}_{1b} \neq 0, \hat{m}_{2b} = 0)$$

where $\alpha$ and $\beta$ are absorptivity ratios, with $\alpha=(A-\nabla_a)/(B-\nabla_b)$ measured in an image stained only with PAP-DAB, and averaged over the entire image, and $\beta=(A-\nabla_a)/(B-\nabla_b)$ measured in an image stained only with hematoxylin and averaged over the entire image. $\alpha$ and $\beta$ were found to be 1.71±0.039 and 0.51±0.007, respectively. $\nabla_a$ and $\nabla_b$ were the average absorbances of unstained tissue at wavelengths $\lambda_a$ and $\lambda_b$, respectively. In doubly labelled tissue sections, attenuation is caused by the tissue itself as well as by the two stains. Assuming that the tissue section itself is translucent and the attenuations at the two wavelengths are $\nabla_a$ and $\nabla_b$, A and B in EQN. 17 were replaced by $A-\nabla_a$ and $B-\nabla_b$, respectively. The tissue absorbancies are very small and appear uniform over the wavelengths used; thus, any errors in the estimation caused by neglecting the tissue absorbancies contribute only small variations to the other measurements. Each of $\hat{m}_{1b}$ and $\hat{m}_{2b}$ (the relative absorptivities of the two stains at wavelength $\lambda_b$) were assumed to be equal to 1.0.

In order to determine the optimum wavelengths to use in the segmentation, equation 14 was rewritten in the form:

$$\sigma^2_{\delta_1}(\lambda_a,\lambda_b) = \frac{\sigma^2(A) + \beta^2\sigma^2(B)}{m^2_{1b}(\alpha - \beta)^2} \quad \text{EQN. 18}$$

$$\sigma^2_{\delta_2}(\lambda_a,\lambda_b) = \frac{\sigma^2(A) + \alpha^2\sigma^2(B)}{m^2_{2b}(\alpha - \beta)^2}$$

$$(\alpha \neq \beta, m_{1b} \neq 0, m_{2b} \neq 0)$$

Since $m_{1b}$ and $m_{2b}$ are unknown, rather than calculating the absolute variances, a variation index which expressed the variance relative to the variances at two standard wavelengths $\lambda_1$ and $\lambda_2$ (in this case 480 nm and 570 nm) was calculated. The variation indices were:

$$\sigma\text{index} - \delta_1^2 = \frac{m^2_{1b}(\lambda_2)}{m^2_{1b}(\lambda_b)} \times \frac{v^2_{\delta_1}(\lambda_a,\lambda_b)}{v^2_{\delta_1}(\lambda_1,\lambda_2)} \quad \text{EQN. 19}$$

$$\sigma\text{index} - \delta_2^2 = \frac{m^2_{2b}(\lambda_2)}{m^2_{2b}(\lambda_b)} \times \frac{v^2_{\delta_2}(\lambda_a,\lambda_b)}{v^2_{\delta_2}(\lambda_1,\lambda_2)}$$

where $v_{\delta_1}^2$ and $v_{\delta_2}^2$ were defined as:

$$v_{\delta_1}^2(\lambda_a,\lambda_b) = \frac{\sigma^2(A) + \beta^2\sigma^2(B)}{(\alpha - \beta)^2} \quad \text{EQN. 20}$$

$$v_{\delta_2}^2(\lambda_a,\lambda_b) = \frac{\sigma^2(A) + \alpha^2\sigma^2(B)}{(\alpha - \beta)^2}$$

$$(\alpha \neq \beta)$$

The optimum wavelengths were determined by minimizing the summation of the variation indices. The optimum wavelengths thus determined were 400 nm and 600 nm. The chromatic aberration in the optical path of the imaging system was minimum at wavelengths between 480 nm and 630 nm. Chromatic aberration was determined from the shift in the image at different wavelengths. In order to obtain a low variance while minimizing chromatic aberration, near-optimum wavelengths of 480 nm and 570 nm were used.

The accuracy of the decomposition method was determined by comparing stain density estimates obtained by decomposing dual-stained tissue samples with estimates obtained from single-stained tissue samples. For PAP-DAB, it was found that coefficient of correlation between stain density estimates obtained from single-stained tissue samples and from decomposition of dual-stained tissue samples was 0.994. The difference between the estimates obtained with the two methods was not significant. For hematoxylin, the coefficient of correlation between stain density estimates obtained from single-stained tissue samples and from decomposition of dual-stained tissue samples was 0.998. Again, the difference was not significant. Accordingly, it was concluded that decomposition of dual-stained images produced accurate estimates of the densities of the individual stains.

EXAMPLE 2

Triple-wavelength segmentation of triple-stained. image

In this example, sample slides labelled with three stains were analyzed. The stains used were PAP-DAB, FastRed, and hematoxylin. Slides were prepared with 1) the combination of PAP-DAB, FastRed and hematoxylin, 2) PAP-DAB alone, 3) FastRed alone, 4) hematoxylin alone, and 5) no stain.

The absorbances measured at wavelengths $\lambda_a$, $\lambda_b$ and $\lambda_c$ were:

$$A(x,y) = \ln\left[\frac{G0_a(x,y)}{G_a(x,y)}\right] \quad \text{EQN. 21}$$

$$B(x,y) = \ln\left[\frac{G0_b(x,y)}{G_b(x,y)}\right]$$

$$C(x,y) = \ln\left[\frac{G0_c(x,y)}{G_c(x,y)}\right]$$

respectively. From EQN. 9, the mass densities of stains 1, 2 and 3 where found to be:

$$\delta_1(x,y) = \frac{(\beta_2 - \gamma_2)A(x,y) + (\gamma_1 - \beta_1)B(x,y) + (\beta_1\gamma_2 - \beta_2\gamma_1)C(x,y)}{\hat{m}_{1c} \cdot [\alpha_1(\beta_2 - \gamma_2) - \alpha_2(\beta_1 - \gamma_1) + (\beta_1\gamma_2 - \gamma_1\beta_2)]} \quad \text{EQN. 22}$$

$$\delta_2(x,y) = \frac{(\gamma_2 - \alpha_2)A(x,y) + (\alpha_1 - \gamma_1)B(x,y) + (\alpha_2\gamma_1 - \alpha_1\gamma_2)C(x,y)}{\hat{m}_{2c} \cdot [\alpha_1(\beta_2 - \gamma_2) - \alpha_2(\beta_1 - \gamma_1) + (\beta_1\gamma_2 - \gamma_1\beta_2)]}$$

$$\delta_3(x,y) = \frac{(\alpha_2 - \beta_2)A(x,y) + (\beta_1 - \alpha_1)B(x,y) + (\alpha_1\beta_2 - \alpha_2\beta_1)C(x,y)}{\hat{m}_{3c} \cdot [\alpha_1(\beta_2 - \gamma_2) - \alpha_2(\beta_1 - \gamma_1) + (\beta_1\gamma_2 - \gamma_1\beta_2)]}$$

$\hat{m}_{1c}$, $\hat{m}_{2c}$ and $\hat{m}_{3c}$, the relative absorptivities of the three stain components at wavelength $\lambda_c$, were assumed to be 1.0.

The absorptivity ratios of PAP-DAB, FastRed, and hematoxylin, were calculated as follows: $\alpha_1=(A-\nabla_a)/(C-\nabla_c)$ measured in the image stained only with PAP-DAB and averaged over all pixels, $\alpha_2=(B-\nabla_b)/(C-\nabla_c)$ measured in the image stained only with PAP-DAB and averaged over all pixels, $\beta_1=(A-\nabla_a)/(C-\nabla_c)$ measured in the image stained only with FastRed and averaged over all pixels, $\beta_2=(B-\nabla_b)/(C-\nabla_c)$ measured in the image stained only with FastRed and averaged over all pixels, $\gamma_1=(A-\nabla_a)/(C-\nabla_c)$ measured in the image stained only with hematoxylin and averaged over all pixels, $\gamma_2=(B-\nabla_b)/(C-\nabla_c)$ measured in the image stained only with hematoxylin and averaged over all pixels. The values obtained for these parameters are shown in Table 4.

TABLE 4

| Absorptivity Ratios | |
|---|---|
| $m_{i\,480}/m_{i\,630}$ | $m_{i\,480}/m_{i\,570}$ |
| $\alpha_1 = 2.44 \pm 0.049$ | $\alpha_2 = 1.42 \pm 0.021$ |
| $\beta_1 = 4.03 \pm 0.052$ | $\beta_2 = 6.39 \pm 0.091$ |
| $\gamma_1 = 0.67 \pm 0.002$ | $\gamma_2 = 1.37 \pm 0.032$ |

$\nabla_a$, $\nabla_b$, and $\nabla_c$, the effective absorbencies of unstained tissue sections at wavelength $\lambda_c$, were calculated from the absorbance of unstained tissue $\ln[G0_a(x,y)/G_a(x,y)]$, averaged over the entire image. Assuming that the tissue section itself is translucent and the attenuations at the three wavelengths are $\nabla_a$, $\nabla_b$, and $\nabla_c$, A,B, and C in EQN. 20 were replaced by $A-\nabla_a$, $B-\nabla_b$ and $C-\nabla_c$, respectively.

The wavelengths which minimized the summation of the variance values were determined. In the three component case, equation 14 was rewritten in the following form to determine the variances:

$$\sigma^2_{\delta_1}(\lambda_a,\lambda_b,\lambda_c) = = \text{EQN. 23}$$

$$\frac{(\beta_2 - \gamma_2)^2\sigma^2(A) + (\gamma_1 - \beta_1)^2\sigma^2(B) + (\beta_1\gamma_2 - \beta_2\gamma_1)^2\sigma^2(C)}{m_{1c}^2 \cdot [\alpha_1(\beta_2 - \gamma_2) - \alpha_2(\beta_1 - \gamma_1) + (\beta_1\gamma_2 - \gamma_1\beta_2)]^2}$$

$$\sigma^2_{\delta_2}(\lambda_a,\lambda_b,\lambda_c) = =$$

$$\frac{(\gamma_2 - \alpha_2)^2\sigma^2(A) + (\alpha_1 - \gamma_1)^2\sigma^2(B) + (\alpha_2\gamma_1 - \alpha_1\gamma_2)^2\sigma^2(C)}{m_{2c}^2 \cdot [\alpha_1(\beta_2 - \gamma_2) - \alpha_2(\beta_1 - \gamma_1) + (\beta_1\gamma_2 - \gamma_1\beta_2)]^2}$$

$$\sigma^2_{\delta_3}(\lambda_a,\lambda_b,\lambda_c) = =$$

$$\frac{(\alpha_2 - \beta_2)^2\sigma^2(A) + (\beta_1 - \alpha_1)^2\sigma^2(B) + (\alpha_1\beta_2 - \alpha_2\beta_1)^2\sigma^2(C)}{m_{3c}^2 \cdot [\alpha_1(\beta_2 - \gamma_2) - \alpha_2(\beta_1 - \gamma_1) + (\beta_1\gamma_2 - \gamma_1\beta_2)]^2}$$

Again, rather than calculating the absolute variances, a variation index which expressed the variation relative to the variations at standard wavelengths $\lambda_1$, $\lambda_2$, and $\lambda_3$ (in this case 480 nm, 570 nm, and 630 nm) was calculated. The variation indices were thus:

$$\sigma^2_{index-\delta_k} = \frac{m_{kc}^2(\lambda_3)}{m_{kc}^2(\lambda_c)} \times \frac{v^2_{\delta_k}(\lambda_a,\lambda_b,\lambda_c)}{v^2_{\delta_k}(\lambda_1,\lambda_2,\lambda_3)} \quad \text{EQN. 24}$$

$(k = 1,2,3)$ where $v_{\delta_1}^2$, $v_{\delta_2}^2$, and $v_{\delta_3}^2$ were defined as:

$$v^2_{\delta_1}(\lambda_a,\lambda_b,\lambda_c) = \quad \text{EQN. 25}$$

-continued $$v_{\delta_2}^2(\lambda_a,\lambda_b,\lambda_c) = $$

$$\frac{(\beta_2-\gamma_2)^2\sigma^2(A)+(\gamma_1-\beta_1)^2\sigma^2(B)+(\beta_1\gamma_2-\beta_2\gamma_1)^2\sigma^2(C)}{[\alpha_1(\beta_2-\gamma_2)-\alpha_2(\beta_1-\gamma_1)+(\beta_1\gamma_2-\gamma_1\beta_2)]^2}$$

$$\frac{(\gamma_2-\alpha_2)^2\sigma^2(A)+(\alpha_1-\gamma_1)^2\sigma^2(B)+(\alpha_2\gamma_1-\alpha_1\gamma_2)^2\sigma^2(C)}{[\alpha_1(\beta_2-\gamma_2)-\alpha_2(\beta_1-\gamma_1)+(\beta_1\gamma_2-\gamma_1\beta_2)]^2}$$

$$v_{\delta_3}^2(\lambda_a,\lambda_b,\lambda_c) = $$

$$\frac{(\alpha_2-\beta_2)^2\sigma^2(A)+(\beta_1-\alpha_1)^2\sigma^2(B)+(\alpha_1\beta_2-\alpha_2\beta_1)^2\sigma^2(C)}{[\alpha_1(\beta_2-\gamma_2)-\alpha_2(\beta_1-\gamma_1)+(\beta_1\gamma_2-\gamma_1\beta_2)]^2}$$

The optimum wavelengths were determined by minimizing the summation of the variation indices. The summation of the variation indices was minimized at 400, 560 and 610 nm. Since the chromatic aberrations in the optical path of the imaging system were minimal between 480 and 630 nm, wavelengths of 480, 570 nm, and 630 nm were used to minimize the overall error.

The accuracy of the triple-wavelength decomposition method was determined by comparing stain density estimates obtained by decomposing triple-stained tissue samples with estimates obtained from single-stained tissue samples. For PAP-DAB, it was found that the coefficient of correlation between stain density estimates obtained from single-stained tissue samples and from decomposition of triple-stained tissue samples was 0.996. For hematoxylin, the coefficient of correlation between stain density estimates obtained from single-stained tissue samples and from decomposition of triple-stained tissue samples was 0.992. For FastRed, the coefficient of correlation between stain density estimates obtained from single-stained tissue samples and from decomposition of triple-stained tissue samples was 0.973. Again, the differences between the estimates obtained from single-stained and triple-stained samples were not significant, and it was concluded that decomposition of triple-stained images produced accurate estimates of the densities of the individual stains.

The practice of the invention is illustrated by the examples given above, which describe the use of invention for analyzing images in which two or three stains were used, and demonstrate the accuracy of the method. The invention may also be used to analyze images in which a larger number of stains are used. The theoretical basis for analysis of images stained with two, three, or more stains has been described, and the method may be used for images stained with more than three stains according to the procedures for image acquisition and analysis described herein.

The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method for analyzing microscope images of multiply stained samples, comprising the steps of:

a) selecting N stains;

b) preparing at least one unstained sample;

c) preparing at least N singly-stained samples, each of said at least N singly-stained samples being stained with a different one of said N stains;

d) preparing at least one multiply-stained sample stained with all of said N stains;

e) selecting N wavelengths of light;

f) acquiring images formed by shining light of each of said N wavelengths through each of said at least one unstained sample, said at least N singly-stained samples, and said at least one multiply-stained sample;

g) determining the absorbance of said at least one unstained sample for each of said N wavelengths of light;

h) determining the absorbance of each of said at least N singly-stained samples for each of said N wavelengths of light;

i) determining the absorbance of said at least one multiply-stained sample for each of said N wavelengths of light;

j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths; wherein step e) comprises the further steps of:

i) estimating the variance $\sigma_{\delta_i}^2$ of the mass density $\delta_i$ for each stain i, from the variance of the absorbances $A_k$ over all wavelengths $\lambda_k$, according to the following equation:

$$\sigma_{\delta_i}^2(\lambda_1,\lambda_2,\ldots,\lambda_N) = \sum_{k=1}^{N}\left[\frac{\partial f(A_{10},A_{20},\ldots,A_{N0})}{\partial A_k}\right]^2 \sigma^2(A_k),$$

wherein $A_{k0}$ is the mean value of $A_k$;

ii) calculating the sum of said variances for each stain i as $$\sum_{i=1}^{N}\sigma_{\delta_i}^2(\lambda_1,\lambda_2,\ldots,\lambda_N);$$

and iii) selecting N wavelengths $\lambda_k$ which minimize said sum of said variances.

2. A method in accordance with claim 1, wherein N equals 2 and wherein said variances are determined as follows:

$$\sigma_{\delta_1}^2(\lambda_a,\lambda_b) = \frac{\sigma^2(A)+\beta^2\sigma^2(B)}{m_{1b}^2(\alpha-\beta)^2}$$

$$\sigma_{\delta_2}^2(\lambda_a,\lambda_b) = \frac{\sigma^2(A)+\alpha^2\sigma^2(B)}{m_{2b}^2(\alpha-\beta)^2}$$

$(\alpha \neq \beta, m_{1b} \neq 0, m_{2b} \neq 0)$ wherein the two wavelengths used are $\lambda_a$ and $\lambda_b$; wherein A is the absorbance at $\alpha_a$ and B is the absorbance at $\alpha_b$; wherein $\alpha$ is the absorptivity ratio for the first stain and $\beta$ is the absorptivity ratio for the second stain; and wherein $m_{1b}$ and $m_{2b}$ are the absorptivities of said first stain and said second stain at $\lambda_b$.

3. A method in accordance with claim 1, wherein N equals 2 and wherein said variances are determined relative to the variances at two predetermined constant wavelengths and expressed as variation indices $\delta\text{index-}\sigma_1^2$ and $\delta\text{index-}\sigma_2^2$, determined according to the following:

$$\sigma\text{index}-\delta_1^2 = \frac{\sigma_{\delta_1}^2(\lambda_a,\lambda_b)}{\sigma_{\delta_1}^2(\lambda_1,\lambda_2)} = \frac{m_{12}^2}{m_{1b}^2} \times \frac{v_{\delta_1}^2(\lambda_a,\lambda_b)}{v_{\delta_1}^2(\lambda_1,\lambda_2)}$$

$$\sigma\text{index}-\delta_2^2 = \frac{\sigma_{\delta_2}^2(\lambda_a,\lambda_b)}{\sigma_{\delta_2}^2(\lambda_1,\lambda_2)} = \frac{m_{22}^2}{m_{2b}^2} \times \frac{v_{\delta_2}^2(\lambda_a,\lambda_b)}{v_{\delta_2}^2(\lambda_1,\lambda_2)}$$

wherein $$v_{\delta_1}^2(\lambda_a,\lambda_b) = \frac{\sigma^2(A) + \beta^2\sigma^2(B)}{(\alpha - \beta)^2}$$

$(\alpha \ne \beta)$ $$v_{\delta_2}^2(\lambda_a,\lambda_b) = \frac{\sigma^2(A) + \alpha^2\sigma^2(B)}{(\alpha - \beta)^2},$$

$$\frac{m_{12}^2}{m_{1b}^2} = \frac{A_{12}^2}{A_{1b}^2} \text{ and } \frac{m_{22}^2}{m_{2b}^2} = \frac{A_{22}^2}{A_{2b}^2},$$

wherein $\lambda_1$ and $\lambda_2$ are predetermined constant wavelengths, and wherein the two wavelengths used are $\lambda_a$ and $\lambda_b$; wherein A is the absorbance of double stained specimens at $\lambda_a$ and B is the absorbance of double stained specimens at $\lambda_b$; wherein $\alpha$ is the absorptivity ratio for the first stain and $\beta$ is the absorptivity ratio for the second stain; wherein $m_{1b}$ and $m_{2b}$ are the absorptivities of said first stain and said second stain at $\lambda_b$, wherein $A_{12}$ is the absorbance of stain 1 at wavelength $\lambda_2$, $A_{1b}$ is the absorbance of stain 1 at wavelength $\lambda_b$, $A_{22}$ is the absorbance of stain 2 at wavelength $\lambda_2$, and $A_{2b}$ is the absorbance of stain 2 at wavelength $\lambda_b$.

4. A method in accordance with claim 1, wherein N equals 3 wherein said variances are calculated accorded to the following equation:

$$\sigma_{\delta_1}^2(\lambda_a,\lambda_b,\lambda_c) = = \frac{(\beta_2 - \gamma_2)^2\sigma^2(A) + (\gamma_1 - \beta_1)^2\sigma^2(B) + (\beta_1\gamma_2 - \beta_2\gamma_1)^2\sigma^2(C)}{m_{1c}^2 \cdot [(\alpha_1(\beta_2 - \gamma_2) - \alpha_2(\beta_1 - \gamma_1) + (\beta_1\gamma_2 - \gamma_1\beta_2)]^2}$$

$$\sigma_{\delta_2}^2(\lambda_a,\lambda_b,\lambda_c) = = \frac{(\gamma_2 - \alpha_2)^2\sigma^2(A) + (\alpha_1 - \gamma_1)^2\sigma^2(B) + (\alpha_2\gamma_1 - \alpha_1\gamma_2)^2\sigma^2(C)}{m_{2c}^2 \cdot [(\alpha_1(\beta_2 - \gamma_2) - \alpha_2(\beta_1 - \gamma_1) + (\beta_1\gamma_2 - \gamma_1\beta_2)]^2}$$

$$\sigma_{\delta_3}^2(\lambda_a,\lambda_b,\lambda_c) = = \frac{(\alpha_2 - \beta_2)^2\sigma^2(A) + (\beta_1 - \alpha_1)^2\sigma^2(B) + (\alpha_1\beta_2 - \alpha_2\beta_1)^2\sigma^2(C)}{m_{3c}^2 \cdot [(\alpha_1(\beta_2 - \gamma_2) - \alpha_2(\beta_1 - \gamma_1) + (\beta_1\gamma_2 - \gamma_1\beta_2)]^2}$$

wherein the three wavelengths used are $\lambda_a$, $\lambda_b$, and $\lambda_c$; wherein A is the absorbance at $\lambda_a$, B is the absorbance at $\lambda_b$ and C is the absorbance at $\lambda_c$; wherein $\alpha_1$, $\beta_1$, and $\gamma_1$ are the absorptivity ratios for the first, second and third stains, respectively, calculated at $\lambda_a$ and $\lambda_c$ and $\alpha_2$, $\beta_2$, and $\lambda_2$ are the absorptivity ratios for the first, second and third stains, respectively, calculated at $\lambda_b$ and $\lambda_c$, and wherein $m_{ic}$ is the absorptivity of stain i at $\lambda_c$.

5. A method in accordance with claim 1, wherein N equals 3 and wherein said variances are determined relative to the variances at three predetermined constant wavelengths and expressed as variation indices $\delta\text{index-}\delta_k^2$ for k=1 to 3, calculated according to the following:

$$\sigma_{\text{index}-\delta_k}^2 = \frac{\sigma_{\delta_k}^2(\lambda_a,\lambda_b,\lambda_c)}{\sigma_{\delta_k}^2(\lambda_1,\lambda_2,\lambda_3)} = \frac{m_{k3}^2}{m_{kc}^2} \times \frac{v_{\delta_k}^2(\lambda_a,\lambda_b,\lambda_c)}{v_{\delta_k}^2(\lambda_1,\lambda_2,\lambda_3)}$$

wherein $v_{\delta_1}^2$, $v_{\delta_2}^2$, and $v_{\delta_3}^2$ are defined as:

$$v_{\delta_1}^2(\lambda_a,\lambda_b,\lambda_c) =$$

$$\frac{(\beta_2 - \gamma_2)^2\sigma^2(A) + (\gamma_1 - \beta_1)^2\sigma^2(B) + (\beta_1\gamma_2 - \beta_2\gamma_1)^2\sigma^2(C)}{[\alpha_1(\beta_2 - \gamma_2) - \alpha_2(\beta_1 - \gamma_1) + (\beta_1\gamma_2 - \gamma_1\beta_2)]^2}$$

$$v_{\delta_2}^2(\lambda_a,\lambda_b,\lambda_c) =$$

$$\frac{(\gamma_2 - \alpha_2)^2\sigma^2(A) + (\alpha_1 - \gamma_1)^2\sigma^2(B) + (\alpha_2\gamma_1 - \alpha_1\gamma_2)^2\sigma^2(C)}{[\alpha_1(\beta_2 - \gamma_2) - \alpha_2(\beta_1 - \gamma_1) + (\beta_1\gamma_2 - \gamma_1\beta_2)]^2}$$

$$v_{\delta_3}^2(\lambda_a,\lambda_b,\lambda_c) =$$

$$\frac{(\alpha_2 - \beta_2)^2\sigma^2(A) + (\beta_1 - \alpha_1)^2\sigma^2(B) + (\alpha_1\beta_2 - \alpha_2\beta_2)^2\sigma^2(C)}{[\alpha_1(\beta_2 - \gamma_2) - \alpha_2(\beta_1 - \gamma_1) + (\beta_1\gamma_2 - \gamma_1\beta_2)]^2}$$

and $$\frac{m_{k3}^2}{m_{kc}^2} = \frac{A_{k3}^2}{A_{kc}^2},$$

wherein $\lambda_1$, $\lambda_2$, and $\lambda_3$ are the predetermined constant wavelengths, wherein the three wavelengths used are $\lambda_a$, $\lambda_b$, and $\lambda_c$; wherein A is the absorbance at $\lambda_a$, B is the absorbance at $\lambda_b$, and C is the absorbance at $\lambda_c$, all determined from triply stained slides; wherein $\alpha_1$, $\beta_1$, and $\gamma_1$ are the absorptivity ratios for the first, second and third stains, respectively, calculated at $\lambda_a$ and $\lambda_c$, and $\alpha_2$, $\beta_2$, and $\gamma_2$ are the absorptivity ratios for the first, second and third stains, respectively, calculated at $\lambda_b$ and $\lambda_c$, wherein $m_{ic}$ is the absorptivity of stain i at $\lambda_c$, wherein $A_{k3}$ is the absorbance of stain k at wavelength $\lambda_3$ and $A_{kc}$ is the absorbance of stain k at wavelength $\lambda_c$.

6. A method for analyzing microscope images of multiply stained samples, comprising the steps of:
   a) selecting N stains;
   b) preparing at least one unstained sample;
   c) preparing at least N singly-stained samples, each of said at least N singly-stained samples being stained with a different one of said N stains;
   d) preparing at least one multiply-stained sample stained with all of said N stains;
   e) selecting N wavelengths of light;
   f) acquiring images formed by shining light of each of said N wavelengths through each of said at least one unstained sample, said at least N singly-stained samples, and said at least one multiply-stained sample;
   g) determining the absorbance of said at least one unstained sample for each of said N wavelengths of light;
   h) determining the absorbance of each of said at least N singly-stained samples for each of said N wavelengths of light;
   i) determining the absorbance of said at least one multiply-stained sample for each of said N wavelengths of light;
   j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths, wherein the density of a stain i at a location (x,y) of a sample is calculated as:

$$\delta_i(x,y) = \frac{\Pi_i(x,y)}{m_{iN} R} \quad (R \neq 0, m_{iN} \neq 0, i = 1, 2, \ldots, N),$$

where $$R = \begin{vmatrix} r_{11} & r_{21} & \cdots & r_{i1} & \cdots & r_{N1} \\ r_{12} & r_{22} & \cdots & r_{i2} & \cdots & r_{N2} \\ \cdot & \cdot & & \cdot & & \cdot \\ \cdot & \cdot & & \cdot & & \cdot \\ r_{1k} & r_{2k} & \cdots & r_{ik} & \cdots & r_{Nk} \\ \cdot & \cdot & & \cdot & & \cdot \\ \cdot & \cdot & & \cdot & & \cdot \\ r_{1(N-1)} & r_{2(N-1)} & \cdots & r_{i(N-1)} & \cdots & r_{N(N-1)} \\ 1 & 1 & \cdots & 1 & \cdots & 1 \end{vmatrix},$$

$$\Pi_1(x,y) = \begin{vmatrix} A_1(x,y) & r_{21} & \cdots & r_{i1} & \cdots & r_{N1} \\ A_2(x,y) & r_{22} & \cdots & r_{i2} & \cdots & r_{N2} \\ \cdot & \cdot & & \cdot & & \cdot \\ \cdot & \cdot & & \cdot & & \cdot \\ A_k(x,y) & r_{2k} & \cdots & r_{ik} & \cdots & r_{NK} \\ \cdot & \cdot & & \cdot & & \cdot \\ \cdot & \cdot & & \cdot & & \cdot \\ A_{N-1}(x,y) & r_{2(N-1)} & \cdots & r_{i(N-1)} & \cdots & r_{N(N-1)} \\ A_N(x,y) & 1 & \cdots & 1 & \cdots & 1 \end{vmatrix},$$

$$\Pi_2(x,y) = \begin{vmatrix} r_{11} & A_1(x,y) & r_{31} & \cdots & r_{i1} & \cdots & r_{N1} \\ r_{12} & A_2(x,y) & r_{32} & \cdots & r_{i2} & \cdots & r_{N2} \\ \cdot & \cdot & \cdot & & \cdot & & \cdot \\ \cdot & \cdot & \cdot & & \cdot & & \cdot \\ r_{1k} & A_k(x,y) & r_{3k} & \cdots & r_{ik} & \cdots & r_{NK} \\ \cdot & \cdot & \cdot & & \cdot & & \cdot \\ \cdot & \cdot & \cdot & & \cdot & & \cdot \\ r_{1(N-1)} & A_{N-1}(x,y) & r_{3(N-1)} & \cdots & r_{i(N-1)} & \cdots & r_{N(N-1)} \\ 1 & A_N(x,y) & 1 & \cdots & 1 & \cdots & 1 \end{vmatrix},$$

$$\Pi_i(x,y) = \begin{vmatrix} r_{11} & \cdots & r_{(i-1)1} & A_1(x,y) & r_{(i+1)1} & \cdots & r_{N1} \\ r_{12} & \cdots & r_{(i-1)2} & A_2(x,y) & r_{(i+1)2} & \cdots & r_{N2} \\ \cdot & & \cdot & \cdot & \cdot & & \cdot \\ \cdot & & \cdot & \cdot & \cdot & & \cdot \\ r_{1k} & \cdots & r_{(i-1)k} & A_k(x,y) & r_{(i+1)k} & \cdots & r_{Nk} \\ \cdot & & \cdot & \cdot & \cdot & & \cdot \\ \cdot & & \cdot & \cdot & \cdot & & \cdot \\ r_{1(N-1)} & \cdots & r_{(i-1)(N-1)} & A_{N-1}(x,y) & r_{(i+1)(N-1)} & \cdots & r_{N(N-1)} \\ 1 & \cdots & 1 & A_N(x,y) & 1 & \cdots & 1 \end{vmatrix},$$

and $$\Pi_N(x,y) = \begin{vmatrix} r_{11} & \cdots & r_{i1} & \cdots & r_{(N-1)1} & A_1(x,y) \\ r_{12} & \cdots & r_{i2} & \cdots & r_{(N-1)2} & A_2(x,y) \\ \cdot & & \cdot & & \cdot & \cdot \\ \cdot & & \cdot & & \cdot & \cdot \\ r_{1k} & \cdots & r_{ik} & \cdots & r_{(N-1)k} & A_k(x,y) \\ \cdot & & \cdot & & \cdot & \cdot \\ \cdot & & \cdot & & \cdot & \cdot \\ r_{1(N-1)} & \cdots & r_{i(N-1)} & \cdots & r_{(N-1)(N-1)} & A_{N-1}(x,y) \\ 1 & \cdots & 1 & \cdots & 1 & A_N(x,y) \end{vmatrix};$$

wherein $r_{ik}$ is the ratio of the absorptivity of stain i at wavelength $\lambda_k$ to the absorptivity of stain i at wavelength $\lambda_N$, $A_k(x,y)$ is the absorbance measured at location (x,y) and wavelength $\lambda_k$, and $m_{iN}$ is the absorptivity of stain i at wavelength $\lambda_N$.

7. A method for analyzing microscope images of multiply stained samples, comprising the steps of:
   a) selecting N stains;
   b) preparing at least one unstained sample;
   c) preparing at least N singly-stained samples, each of said at least N singly-stained samples being stained with a different one of said N stains;
   d) preparing at least one multiply-stained sample stained with all of said N stains;
   e) selecting N wavelengths of light;
   f) acquiring images formed by shining light of each of said N wavelengths through each of said at least one unstained sample, said at least N singly-stained samples, and said at least one multiply-stained sample;
   g) determining the absorbance of said at least one unstained sample for each of said N wavelengths of light;
   h) determining the absorbance of each of said at least N singly-stained samples for each of said N wavelengths of light;
   i) determining the absorbance of said at least one multiply-stained sample for each of said N wavelengths of light;

j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths, wherein the density of a stain i at a location (x,y) of a sample is calculated as:

$$\delta_i(x,y) = \frac{\Pi_i(x,y)}{m_{iN} R} \quad (R \neq 0, m_{iN} \neq 0, i = 1, 2, \ldots, N),$$

where $$R = \begin{vmatrix} r_{11} & r_{21} & \cdots & r_{i1} & \cdots & r_{N1} \\ r_{12} & r_{22} & \cdots & r_{i2} & \cdots & r_{N1} \\ \cdot & & & & & \\ \cdot & & & & & \\ \cdot & & & & & \\ r_{1k} & r_{2k} & \cdots & r_{ik} & \cdots & r_{Nk} \\ \cdot & & & & & \\ \cdot & & & & & \\ \cdot & & & & & \\ r_{1(N-1)} & r_{2(N-1)} & \cdots & r_{i(N-1)} & \cdots & r_{N(N-1)} \\ 1 & 1 & \cdots & 1 & \cdots & 1 \end{vmatrix},$$

$$\Pi_1(x,y) = \begin{vmatrix} A_1(x,y) & r_{21} & \cdots & r_{i1} & \cdots & r_{N1} \\ A_2(x,y) & r_{22} & \cdots & r_{i2} & \cdots & r_{N2} \\ \cdot & & & & & \\ \cdot & & & & & \\ \cdot & & & & & \\ A_k(x,y) & r_{2k} & \cdots & r_{ik} & \cdots & r_{NK} \\ \cdot & & & & & \\ \cdot & & & & & \\ \cdot & & & & & \\ A_{N-1}(x,y) & r_{2(N-1)} & \cdots & r_{i(N-1)} & \cdots & r_{N(N-1)} \\ A_N(x,y) & 1 & \cdots & 1 & \cdots & 1 \end{vmatrix},$$

$$\Pi_2(x,y) = \begin{vmatrix} r_{11} & A_1(x,y) & r_{31} & \cdots & r_{i1} & \cdots & r_{N1} \\ r_{12} & A_2(x,y) & r_{32} & \cdots & r_{i2} & \cdots & r_{N2} \\ \cdot & & & & & & \\ \cdot & & & & & & \\ \cdot & & & & & & \\ r_{1k} & A_k(x,y) & r_{3k} & \cdots & r_{ik} & \cdots & r_{NK} \\ \cdot & & & & & & \\ \cdot & & & & & & \\ \cdot & & & & & & \\ r_{1(N-1)} & A_{N-1}(x,y) & r_{3(N-1)} & \cdots & r_{i(N-1)} & \cdots & r_{N(N-1)} \\ 1 & A_N(x,y) & 1 & \cdots & 1 & \cdots & 1 \end{vmatrix},$$

$$\Pi_i(x,y) = \begin{vmatrix} r_{11} & \cdots & r_{(i-1)1} & A_1(x,y) & r_{(i+1)1} & \cdots & r_{N1} \\ r_{12} & \cdots & r_{(i-1)2} & A_2(x,y) & r_{(i+1)2} & \cdots & r_{N2} \\ \cdot & & & & & & \\ \cdot & & & & & & \\ \cdot & & & & & & \\ r_{1k} & \cdots & r_{(i-1)k} & A_k(x,y) & r_{(i+1)k} & \cdots & r_{Nk} \\ \cdot & & & & & & \\ \cdot & & & & & & \\ \cdot & & & & & & \\ r_{1(N-1)} & \cdots & r_{(i-1)(N-1)} & A_{N-1}(x,y) & r_{(i+1)(N-1)} & \cdots & r_{N(N-1)} \\ 1 & \cdots & 1 & A_N(x,y) & 1 & \cdots & 1 \end{vmatrix},$$

and $$\Pi_N(x,y) = \begin{vmatrix} r_{11} & \cdots & r_{i1} & \cdots & r_{(N-1)1} & A_1(x,y) \\ r_{12} & \cdots & r_{i2} & \cdots & r_{(N-1)2} & A_2(x,y) \\ \cdot & & & & & \\ \cdot & & & & & \\ \cdot & & & & & \\ r_{1k} & \cdots & r_{ik} & \cdots & r_{(N-1)k} & A_k(x,y) \\ \cdot & & & & & \\ \cdot & & & & & \\ \cdot & & & & & \\ r_{1(N-1)} & \cdots & r_{i(N-1)} & \cdots & r_{(N-1)(N-1)} & A_{(N-1)}(x,y) \\ 1 & \cdots & 1 & \cdots & 1 & A_N(x,y) \end{vmatrix};$$

wherein $r_{ik}$ is the ratio of the absorptivity of stain i at wavelength $\lambda_k$ to the absorptivity of stain i at wavelength $\lambda_N$, $A_k(x,y)$ is the absorbance measured at location (x,y) and wavelength $\lambda_k$, and $m_{iN}$ is the absorptivity of stain i at wavelength $\lambda_N$;

wherein said N wavelengths selected in step e) are selected such that the summation of the wavelength-dependent variances of said mass densities of said N stains, $$\sum_{i=1}^{N} \sigma_{\delta_i}^2(\lambda_1, \lambda_2, \ldots \lambda_N),$$

is minimized.

8. A method for analyzing microscope images of multiply stained samples, comprising the steps of:
a) selecting N stains;
b) preparing at least one unstained sample;
c) preparing at least N singly-stained samples, each of said at least N singly-stained samples being stained with a different one of said N stains;
d) preparing at least one multiply-stained sample stained with all of said N stains;
e) selecting N wavelengths of light;
f) acquiring images formed by shining light of each of said N wavelengths through each of said at least one unstained sample, said at least N singly-stained samples, and said at least one multiply-stained sample;
g) determining the absorbance of said at least one unstained sample for each of said N wavelengths of light;
h) determining the absorbance of each of said at least N singly-stained samples for each of said N wavelengths of light;

i) determining the absorbance of said at least one multiply-stained sample for each of said N wavelengths of light;

j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths, wherein the density of a stain $i$ at a location $(x,y)$ of a sample is calculated as:

$$\delta_i(x,y) = \frac{\Pi_i(x,y)}{m_{iN}R} \quad (R \neq 0, m_{iN} \neq 0, i = 1, 2, \ldots, N),$$

where $$R = \begin{vmatrix} r_{11} & r_{21} & \cdots & r_{i1} & \cdots & r_{N1} \\ r_{12} & r_{22} & \cdots & r_{i2} & \cdots & r_{N1} \\ \cdot & & & & & \cdot \\ \cdot & & & & & \cdot \\ r_{1k} & r_{2k} & \cdots & r_{ik} & \cdots & r_{Nk} \\ \cdot & & & & & \cdot \\ \cdot & & & & & \cdot \\ r_{1(N-1)} & r_{2(N-1)} & \cdots & r_{i(N-1)} & \cdots & r_{N(N-1)} \\ 1 & 1 & \cdots & 1 & \cdots & 1 \end{vmatrix},$$

$$\Pi_1(x,y) = \begin{vmatrix} A_1(x,y) & r_{21} & \cdots & r_{i1} & \cdots & r_{N1} \\ A_2(x,y) & r_{22} & \cdots & r_{i2} & \cdots & r_{N2} \\ \cdot & & & & & \cdot \\ \cdot & & & & & \cdot \\ A_k(x,y) & r_{2k} & \cdots & r_{ik} & \cdots & r_{NK} \\ \cdot & & & & & \cdot \\ \cdot & & & & & \cdot \\ A_{N-1}(x,y) & r_{2(N-1)} & \cdots & r_{i(N-1)} & \cdots & r_{N(N-1)} \\ A_N(x,y) & 1 & \cdots & 1 & \cdots & 1 \end{vmatrix},$$

$$\Pi_2(x,y) = \begin{vmatrix} r_{11} & A_1(x,y) & r_{31} & \cdots & r_{i1} & \cdots & r_{N1} \\ r_{12} & A_2(x,y) & r_{32} & \cdots & r_{i2} & \cdots & r_{N2} \\ \cdot & \cdot & & & & & \cdot \\ \cdot & \cdot & & & & & \cdot \\ r_{1k} & A_k(x,y) & r_{3k} & \cdots & r_{ik} & \cdots & r_{NK} \\ \cdot & \cdot & & & & & \cdot \\ \cdot & \cdot & & & & & \cdot \\ r_{1(N-1)} & A_{N-1}(x,y) & r_{3(N-1)} & \cdots & r_{i(N-1)} & \cdots & r_{N(N-1)} \\ 1 & A_N(x,y) & 1 & \cdots & 1 & \cdots & 1 \end{vmatrix},$$

$$\Pi_i(x,y) = \begin{vmatrix} r_{11} & \cdots & r_{(i-1)1} & A_1(x,y) & r_{(i+1)1} & \cdots & r_{N1} \\ r_{12} & \cdots & r_{(i-1)2} & A_2(x,y) & r_{(i+1)2} & \cdots & r_{N2} \\ \cdot & & \cdot & \cdot & \cdot & & \cdot \\ \cdot & & \cdot & \cdot & \cdot & & \cdot \\ r_{1k} & \cdots & r_{(i-1)k} & A_k(x,y) & r_{(i+1)k} & \cdots & r_{Nk} \\ \cdot & & \cdot & \cdot & \cdot & & \cdot \\ \cdot & & \cdot & \cdot & \cdot & & \cdot \\ r_{1(N-1)} & \cdots & r_{(i-1)(N-1)} & A_{N-1}(x,y) & r_{(i+1)(N-1)} & \cdots & r_{N(N-1)} \\ 1 & \cdots & 1 & A_N(x,y) & 1 & \cdots & 1 \end{vmatrix},$$

and $$\Pi_N(x,y) = \begin{vmatrix} r_{11} & \cdots & r_{i1} & \cdots & r_{(N-1)1} & A_1(x,y) \\ r_{12} & \cdots & r_{i2} & \cdots & r_{(N-1)2} & A_2(x,y) \\ \cdot & & \cdot & & \cdot & \cdot \\ \cdot & & \cdot & & \cdot & \cdot \\ r_{1k} & \cdots & r_{ik} & \cdots & r_{(N-1)k} & A_k(x,y) \\ \cdot & & \cdot & & \cdot & \cdot \\ \cdot & & \cdot & & \cdot & \cdot \\ r_{1(N-1)} & \cdots & r_{i(N-1)} & \cdots & r_{(N-1)(N-1)} & A_{(N-1)}(x,y) \\ 1 & \cdots & 1 & \cdots & 1 & A_N(x,y) \end{vmatrix};$$

wherein $r_{ik}$ is the ratio of the absorptivity of stain $i$ at wavelength $\lambda_k$ to the absorptivity of stain $i$ at wavelength $\lambda_N$, $A_k(x,y)$ is the absorbance measured at location $(x,y)$ and wavelength $\lambda_k$, and $m_{iN}$ is the absorptivity of stain $i$ at wavelength $\lambda_N$;

wherein said N wavelengths selected in step e) are selected such that the chromatic aberration in the optical path of the imaging system used to acquire said images is minimized.

9. A method for analyzing microscope images of multiply stained samples, comprising the steps of:

a) selecting N stains;

b) preparing at least one unstained sample;

c) preparing at least N singly-stained samples, each of said at least N singly-stained samples being stained with a different one of said N stains;

d) preparing at least one multiply-stained sample stained with all of said N stains;

e) selecting N wavelengths of light;

f) acquiring images formed by shining light of each of said N wavelengths through each of said at least one unstained sample, said at least N singly-stained samples, and said at least one multiply-stained sample;

g) determining the absorbance of said at least one unstained sample for each of said N wavelengths of light;

h) determining the absorbance of each of said at least N singly-stained samples for each of said N wavelengths of light;

i) determining the absorbance of said at least one multiply-stained sample for each of said N wavelengths of light;

j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths, wherein the density of a stain i at a location (x,y) of a sample is calculated as:

$$\delta_i(x,y) = \frac{\Pi_i(x,y)}{m_{iN} R} \quad (R \neq 0, m_{iN} \neq 0, i = 1, 2, \ldots, N),$$

where $$R = \begin{vmatrix} r_{11} & r_{21} & \cdots & r_{i1} & \cdots & r_{N1} \\ r_{12} & r_{22} & \cdots & r_{i2} & \cdots & r_{N1} \\ \cdot & & & \cdot & & \cdot \\ \cdot & & & \cdot & & \cdot \\ r_{1k} & r_{2k} & \cdots & r_{ik} & \cdots & r_{Nk} \\ \cdot & & & \cdot & & \cdot \\ \cdot & & & \cdot & & \cdot \\ r_{1(N-1)} & r_{2(N-1)} & \cdots & r_{i(N-1)} & \cdots & r_{N(N-1)} \\ 1 & 1 & \cdots & 1 & \cdots & 1 \end{vmatrix},$$

$$\Pi_1(x,y) = \begin{vmatrix} A_1(x,y) & r_{21} & \cdots & r_{i1} & \cdots & r_{N1} \\ A_2(x,y) & r_{22} & \cdots & r_{i2} & \cdots & r_{N2} \\ \cdot & & & \cdot & & \cdot \\ \cdot & & & \cdot & & \cdot \\ A_k(x,y) & r_{2k} & \cdots & r_{ik} & \cdots & r_{NK} \\ \cdot & & & \cdot & & \cdot \\ \cdot & & & \cdot & & \cdot \\ A_{N-1}(x,y) & r_{2(N-1)} & \cdots & r_{i(N-1)} & \cdots & r_{N(N-1)} \\ A_N(x,y) & 1 & \cdots & 1 & \cdots & 1 \end{vmatrix},$$

$$\Pi_2(x,y) = \begin{vmatrix} r_{11} & A_1(x,y) & r_{31} & \cdots & r_{i1} & \cdots & r_{N1} \\ r_{12} & A_2(x,y) & r_{32} & \cdots & r_{i2} & \cdots & r_{N2} \\ \cdot & \cdot & \cdot & & \cdot & & \cdot \\ \cdot & \cdot & \cdot & & \cdot & & \cdot \\ r_{1k} & A_k(x,y) & r_{3k} & \cdots & r_{ik} & \cdots & r_{NK} \\ \cdot & \cdot & \cdot & & \cdot & & \cdot \\ \cdot & \cdot & \cdot & & \cdot & & \cdot \\ r_{1(N-1)} & A_{N-1}(x,y) & r_{3(N-1)} & \cdots & r_{i(N-1)} & \cdots & r_{N(N-1)} \\ 1 & A_N(x,y) & 1 & \cdots & 1 & \cdots & 1 \end{vmatrix},$$

$$\Pi_i(x,y) = \begin{vmatrix} r_{11} & \cdots & r_{(i-1)1} & A_1(x,y) & r_{(i+1)1} & \cdots & r_{N1} \\ r_{12} & \cdots & r_{(i-1)2} & A_2(x,y) & r_{(i+1)2} & \cdots & r_{N2} \\ \cdot & & \cdot & \cdot & \cdot & & \cdot \\ \cdot & & \cdot & \cdot & \cdot & & \cdot \\ r_{1k} & \cdots & r_{(i-1)k} & A_k(x,y) & r_{(i+1)k} & \cdots & r_{Nk} \\ \cdot & & \cdot & \cdot & \cdot & & \cdot \\ \cdot & & \cdot & \cdot & \cdot & & \cdot \\ r_{1(N-1)} & & r_{(i-1)(N-1)} & A_{N-1}(x,y) & r_{(i+1)(N-1)} & \cdots & r_{N(N-1)} \\ 1 & \cdots & 1 & A_N(x,y) & 1 & \cdots & 1 \end{vmatrix},$$

and $$\Pi_N(x,y) = \begin{vmatrix} r_{11} & \cdots & r_{i1} & \cdots & r_{(N-1)1} & A_1(x,y) \\ r_{12} & \cdots & r_{i2} & \cdots & r_{(N-1)2} & A_2(x,y) \\ \cdot & & \cdot & & \cdot & \cdot \\ \cdot & & \cdot & & \cdot & \cdot \\ r_{1k} & \cdots & r_{ik} & \cdots & r_{(N-1)k} & A_k(x,y) \\ \cdot & & \cdot & & \cdot & \cdot \\ \cdot & & \cdot & & \cdot & \cdot \\ r_{1(N-1)} & & r_{i(N-1)} & & r_{(N-1)(N-1)} & A_{(N-1)}(x,y) \\ 1 & \cdots & 1 & \cdots & 1 & A_N(x,y) \end{vmatrix};$$

wherein $r_{ik}$ is the ratio of the absorptivity of stain i at wavelength $\lambda_k$ to the absorptivity of stain i at wavelength $\lambda_N$, $A_k(x,y)$ is the absorbance measured at location (x,y) and wavelength $\lambda_k$, and $m_{iN}$ is the absorptivity of stain i at wavelength $\lambda_N$;

wherein said N wavelengths selected in step e) are selected such that the summation of the wavelength-dependent variances of said mass densities of said N stains, $$\sum_{i=1}^{N} \sigma_{\delta_i}^2(\lambda_1, \lambda_2, \ldots \lambda_N),$$

and the chromatic aberration in the optical path of the imaging system used to acquire said images are minimized.

10. A method for analyzing microscope images of multiply stained samples, comprising the steps of:

a) selecting N stains;
b) preparing at least one unstained sample;
c) preparing at least N singly-stained samples, each of said at least N singly-stained samples being stained with a different one of said N stains;
d) preparing at least one multiply-stained sample stained with all of said N stains;
e) selecting N wavelengths of light;
f) acquiring images formed by shining light of each of said N wavelengths through each of said at least one unstained sample, said at least N singly-stained samples, and said at least one multiply-stained sample;
g) determining the absorbance of said at least one unstained sample for each of said N wavelengths of light;

h) determining the absorbance of each of said at least N singly-stained samples for each of said N wavelengths of light;

i) determining the absorbance of said at least one multiply-stained sample for each of said N wavelengths of light;

j) determining the absorptivity ratio of each of said at least N singly-stained samples at each of said N wavelengths of light by dividing the absorbance measured at each of said N wavelengths by the absorbance measured at a selected one of said N wavelengths, wherein the absorptivity is non-zero for each stain component at said selected one wavelength;

k) determining the mass density of each of said N stains in said at least one multiply-stained sample from said absorbances of said at least one multiply-stained sample at each of said N wavelengths and from said absorptivity ratios of said at least N singly stained samples at each of said N wavelengths;

wherein N=3; wherein step e) comprises the further steps of:

i) estimating the variance $\sigma_{\delta_i}^2$ of the mass density $\delta_i$ for each stain i, from the variance of the absorbances $A_k$ over all wavelengths $\lambda_k$, according to the following equation;

$$\sigma_{\delta_i}^2(\lambda_1,\lambda_2,\lambda_3) = \sum_{k=1}^{3} \left[ \frac{\partial f(A_{10},A_{20},A_{30})}{\partial A_k} \right]^2 \sigma^2(A_k),$$

wherein $A_{k0}$ is the mean value of $A_k$;

ii) calculating the sum of said variances for each stain i as $$\sum_{i=1}^{3} \sigma_{\delta_i}^2(\lambda_1,\lambda_2,\lambda_3);$$

and iii) selecting 3 wavelengths $\lambda_k$ which minimize said sum of said variances;

and wherein and said mass density is determined in step k) according to the following equations:

$$\delta_1(x,y) = \frac{(\beta_2 - \gamma_2)A(x,y) + (\gamma_1 - \beta_1)B(x,y) + (\beta_1\gamma_2 - \beta_2\gamma_1)C(x,y)}{\hat{m}_{1c} \cdot [\alpha_1(\beta_2 - \gamma_2) - \alpha_2(\beta_1 - \gamma_1) + (\beta_1\gamma_2 - \gamma_1\beta_2)]}$$

$$\delta_2(x,y) = \frac{(\gamma_2 - \alpha_2)A(x,y) + (\alpha_1 - \gamma_1)B(x,y) + (\alpha_2\gamma_1 - \alpha_1\gamma_2)C(x,y)}{\hat{m}_{2c} \cdot [\alpha_1(\beta_2 - \gamma_2) - \alpha_2(\beta_1 - \gamma_1) + (\beta_1\gamma_2 - \gamma_1\beta_2)]}$$

$$\delta_3(x,y) = \frac{(\alpha_2 - \beta_2)A(x,y) + (\beta_1 - \alpha_1)B(x,y) + (\alpha_1\beta_2 - \alpha_2\beta_1)C(x,y)}{\hat{m}_{3c} \cdot [\alpha_1(\beta_2 - \gamma_2) - \alpha_2(\beta_1 - \gamma_1) + (\beta_1\gamma_2 - \gamma_1\beta_2)]}$$

wherein $\delta_1(x,y)$ is the density of the first stain, $\delta_2(x,y)$ is the density of the second stain, and $\delta_3(x,y)$ is the density of the third stain at location (x,y) of said multiply stained sample; wherein A(x,y) is the absorbance at the first wavelength, B(x,y) is the absorbance at the second wavelength, and C(x,y) is the absorbance at the third wavelength at location (x,y) of said multiply stained sample; wherein $\alpha_1$, $\beta_1$ and $\gamma_1$ are the absorptivity ratios of said first, second and third stains calculated at said first and third wavelengths and $\alpha_2$, $\beta_2$ and $\gamma_2$ are the absorptivity ratios of said first, second and third stains calculated at said second and third wavelengths; and wherein $\hat{m}_{1c}$, $\hat{m}_{2c}$, and $\hat{m}_{3c}$ are each equal to one or any arbitrary value.

* * * * *